(12) United States Patent
Hyder et al.

(10) Patent No.: US 10,143,686 B2
(45) Date of Patent: Dec. 4, 2018

(54) OXIDOSQUALENE CYCLASE AS A PROTEIN TARGET FOR ANTICANCER THERAPEUTICS

(75) Inventors: Salman M. Hyder, Columbia, MO (US); Yayun Liang, Columbia, MO (US); Xiaoqin Zou, Columbia, MO (US); Sam Z. Grinter, Columbia, MO (US); Sheng-You Huang, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 146 days.

(21) Appl. No.: 13/976,635

(22) PCT Filed: Dec. 22, 2011

(86) PCT No.: PCT/US2011/066797
§ 371 (c)(1), (2), (4) Date: Sep. 18, 2013

(87) PCT Pub. No.: WO2012/092114
PCT Pub. Date: Jul. 5, 2012

(65) Prior Publication Data
US 2014/0005187 A1 Jan. 2, 2014

Related U.S. Application Data

(60) Provisional application No. 61/628,324, filed on Oct. 28, 2011, provisional application No. 61/460,167, filed on Dec. 27, 2010.

(51) Int. Cl.
*A61K 31/452* (2006.01)
*A61K 31/135* (2006.01)
(Continued)

(52) U.S. Cl.
CPC .......... *A61K 31/452* (2013.01); *A61K 31/12* (2013.01); *A61K 31/135* (2013.01);
(Continued)

(58) Field of Classification Search
CPC .............................. A61K 31/357; A61K 38/16
See application file for complete search history.

(56) References Cited

U.S. PATENT DOCUMENTS 6,346,545 B1 * 2/2002 Maier et al. ................. 514/478
8,227,434 B1 * 7/2012 Dalton et al. ............... 514/44 A
(Continued)

FOREIGN PATENT DOCUMENTS

CN 1468220 A 1/2004
CN 103596570 A 2/2014
(Continued)

OTHER PUBLICATIONS

Kahlid, S., et al., Evidence for a tumor promoting effect of high-fat diet independent of insulin resistance in HER2/Neu mammary carcinogenesis. Breast Cancer Res Treat (2010) 122:647-659.*
(Continued)

*Primary Examiner* — San Ming R Hui
(74) *Attorney, Agent, or Firm* — Tracey S. Truitt; Armstrong Teasdale LLP

(57) ABSTRACT

Disclosed herein is a new and improved therapy for the treatment of cancer, which comprises the step of altering cell membrane lipid composition by treating a cancer cell with an enzyme inhibitor which inhibits enzymes regulating the cholesterol biosynthetic pathway. One preferred protein target in the cholesterol biosynthetic pathway to inhibit is oxidosqualene cyclase. In some forms, inhibitors of one or more pathways are combined with an existing chemotherapeutic agent to combat drug resistance and enhance the therapeutic efficacy of conventional therapy.

24 Claims, 16 Drawing Sheets

(51) Int. Cl.

| | | |
|---|---|---|
| *A61K 31/138* | (2006.01) | |
| *A61K 31/343* | (2006.01) | |
| *A61K 31/381* | (2006.01) | |
| *A61K 31/416* | (2006.01) | |
| *A61K 31/423* | (2006.01) | |
| *A61K 31/428* | (2006.01) | |
| *A61K 31/44* | (2006.01) | |
| *A61K 31/4425* | (2006.01) | |
| *A61K 31/4439* | (2006.01) | |
| *A61K 31/536* | (2006.01) | |
| *A61K 31/5685* | (2006.01) | |
| *C12Q 1/26* | (2006.01) | |
| *C12Q 1/533* | (2006.01) | |
| *G01N 33/50* | (2006.01) | |
| *A61K 31/12* | (2006.01) | |

(52) U.S. Cl.
CPC .......... *A61K 31/138* (2013.01); *A61K 31/343* (2013.01); *A61K 31/381* (2013.01); *A61K 31/416* (2013.01); *A61K 31/423* (2013.01); *A61K 31/428* (2013.01); *A61K 31/44* (2013.01); *A61K 31/4425* (2013.01); *A61K 31/4439* (2013.01); *A61K 31/536* (2013.01); *A61K 31/5685* (2013.01); *C12Q 1/26* (2013.01); *C12Q 1/533* (2013.01); *G01N 33/5011* (2013.01); *G01N 2333/904* (2013.01); *G01N 2333/99* (2013.01)

(56) References Cited

U.S. PATENT DOCUMENTS

| | | | |
|---|---|---|---|
| 2002/0068753 A1 | 6/2002 | Ackermann | |
| 2003/0032578 A1* | 2/2003 | Jackson et al. | ................ 514/1 |
| 2010/0092479 A1 | 4/2010 | Johansen | |
| 2014/0221353 A1 | 8/2014 | De Medina | |

FOREIGN PATENT DOCUMENTS

| | | |
|---|---|---|
| EP | 1498482 A2 | 1/2005 |
| EP | 2658544 | 11/2013 |
| WO | 9418961 A1 | 9/1994 |
| WO | 0236584 A1 | 5/2002 |
| WO | 2010149941 A1 | 12/2010 |
| WO | 2013059772 A1 | 4/2013 |
| WO | 2014004854 A1 | 1/2014 |
| WO | 2014042544 A1 | 3/2014 |

OTHER PUBLICATIONS

Bruger, M. et al., Relation of the Plasma Cholesterol to Obesity and to Some of the Complicating Degenerative Diseases. Arch Intern Med (Chic). 1934;53(3):423-434.*
Mark, M. et al., Effects of a novel 2,3-oxidosqualene cyclase inhibitor on the regulation of cholesterol biosynthesis in HepG2 cells. Journal of Lipid Research vol. 37, 1996, p. 148-158.*
Gasco, M. et al., The p53 pathway in breast cancer, Breast Cancer Res 2002, 4:70-76 Available online http://breast-cancer-research.com/content/4/2/070.*
Basu, S. et al., Comparison of triple-negative and estrogen receptorpositive/ progesterone receptor-positive/HER2-negative breast carcinoma using quantitative fluorine-18 fluorodeoxyglucose/positron emission tomography imaging parameters: a potentially useful method for disease characterization. Cancer. Mar. 1, 2008;112(5):995-1000.*
Peffley, D.M. et al., Down-regulation of 3-Hydroxy-3-methylglutaryl Coenzyme A Reductase mRNA Levels and Synthesis in Syrian Hamster C100 Cells by the Oxidosqualene Cyclase Inhibitor [49-(6-allyl-ethyl-amino-hexyloxy)-29-fluoro-phenyl]-(4-bromophenyl)-methanone (Ro 48-8071): Comparison to Simvastatin. Biochemical Pharmacology, vol. 56, pp. 439-449.*
Koopman et al., Blood, vol. 84, No. 5 (September I), 1994: pp. 1415-1420.*
Rakha, et al., Cancer Jan. 1, 2007 / vol. 109 / No. 1, p. 25-32.*
Campbell, et al., Cancer Res. 2006; 66: (17). Sep. 1, 2006.*
Jim Clark, 2007, http://www.chemguide.co.uk/organicprops/aminoacids/enzymes.html.*
Miettinen, Circulation, vol. XLIV, Nov. 1971, p. 842-850.*
Huff et al., Trends in Pharmacological Sciences vol. 26, No. 7, Jul. 2005.*
International Search Report and Written Opinion dated Nov. 13, 2013 from related International application No. PCT/US2013/048231, 16 pgs.
Owens, Chemical combinations elucidate pathway interactions and regulation relevant to Hepatitis C replication, Molecular Systems Biology, 2010, 13 pgs, vol. 6, Article No. 375.
Lenhart, Crystal structure of a squalence cyclase incomplex with the potential anticholesteremic drug Ro48-8071, Chemistry & Biology, 2002, pp. 639-645, vol. 9.
Mejia-Pous, Cholesterol synthesis-related enzyme oxidosqualene cyclase is required to maintain self-renewal in primary erythroid progenitors, Cell Proliferation, 2001, pp. 441-452, vol. 44.
CN Office action summary from related CN Application No. 2011800632241 dated Sep. 8, 2015, 7 pgs.
Morand, Ro 48-8071, a new 2,3-oxidosqualene:lanosterol cyclase inhibitor lowering plasma cholesterol in hamsters, squirrel monkeys, and minipigs: Comparison to simvastatin, J Lipid Res., Feb. 28, 1997, pp. 373-390, vol. 38, No. 2.
CN Office action summary from related CN Application No. 2011800632241 dated Oct. 16, 2014, 5 pgs.
Campbell, Breast Cancer Growth Prevention by Statins', Cancer Res., Sep. 1, 2006, pp. 8707-8714, vol. 66, No. 17.
Desai, Evaluation of the effect of genetic variation on the relationship between statins, cardiovascular disease and cancer, Int J Mol Epidemiol Genet, 2013, pp. 183-192, vol. 4(4).
Dale, Statins and Cancer Risk A Meta-analysis, JAMA, Jan. 4, 2006, pp. 74-80, vol. 295, No. 1.
Jafri, Baseline and On-Treatment High-Density Lipoprotein Cholesterol and the Risk of Cancer in Randomized Controlled Trials of Lipid-Altering Therapy, JACC, Jun. 22, 2010, pp. 2846-2854, vol. 55, No. 25
Supplementary European Search Report from related EP Application No. 11853116.9 dated Apr. 29, 2014, 20 pgs.
Klawitter, Effects of lovastatin on breast cancer cells: a proteometabonomic study, Breast Cancer Research, Mar. 5, 2010, 20 pgs, vol. 12, No. 2.
Atif, Effect of phytosterols on cholesterol metabolism and MAP kinase in MDA-MB-231 human breast cancer cells, The Journal of Nutritional Biochemistry, Feb. 1, 2003, pp. 111-119, vol. 14, No. 2.
Buchwald, Cholesterol Inhibition, Cancer, and Chemotherapy, The Lancet, May 9, 1992, pp. 1154-1156, vol. 339, No. 8802.
Hyder, PRIMA-1 inhibits growth of breast cancer cells by re-activating mutant p53 protein, International Journal of Oncology, Sep. 15, 2009, pp. 1015-1023, vol. 35, No. 05.
Lee, Expression proteomics to p53 mutation reactivation with PRIMA-1 in breast cancer cells, Biochemical and Biophysical Research Communications, Oct. 27, 2006, pp. 1117-1124, vol. 349, No. 3.
Wiklund, Cytotoxic effects of antipsychotic drugs implicate cholesterol homeostasis as a novel chemotherapeutic target, Jan. 1, 2010, pp. 28-40, vol. 125, No. 1.
Grinter, An inverse docking approach for identifying new potential anti-cancer targets, Jan. 6, 2011, pp. 795-799, vol. 29, No. 6.
Examination Report dated May 29, 2015 from related European Application No. 11853116.9, 12 pgs.
Examination Report from related Australian Application No. dated Oct. 29, 2014, 5 pgs.

* cited by examiner

Fig. 8A
Fig. 8B
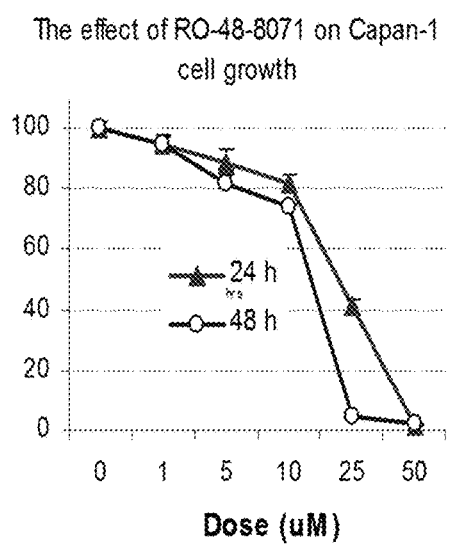
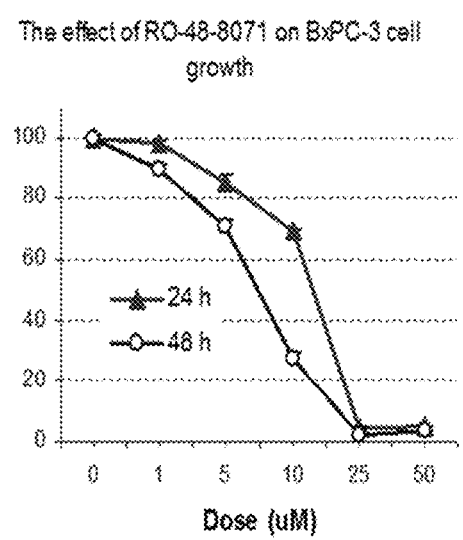

Estrogen, progesterone, and HER-2/neu receptors positive cell lines

Estrogen, progesterone, and HER-2/neu receptors negative cell lines

OXIDOSQUALENE CYCLASE AS A PROTEIN TARGET FOR ANTICANCER THERAPEUTICS

This application claims the benefit of priority of U.S. provisional applications No. 61/460,167, filed on Dec. 27, 2010, and No. 61/628,324, filed Oct. 28, 2011, the disclosures of which are hereby incorporated by reference as if written herein in their entirety.

GRANT STATEMENT

The invention was made with Government support under Grants No. R21GM088517, R56CA86916, and T15LM07089 awarded by the National Institutes of Health. The US Government has certain rights in the invention.

Disclosed herein are anticancer pharmaceuticals and treatments, more specifically to a new protein target, along with inhibitors thereof, for the treatment of cancer.

OSC and its Inhibitors.

The enzyme oxidosqualene cyclase ('OSC') is known to be a part of the cholesterol biosynthetic pathway, whereby OSC converts oxidosqualene to lanosterol forming the steroid scaffold.[1,2] Numerous inhibitors for OSC have been reported, including a series of inhibitors containing a tertiary amine, a hexyloxy spacer and an unrestrained bromophenyl group, such as Formula I

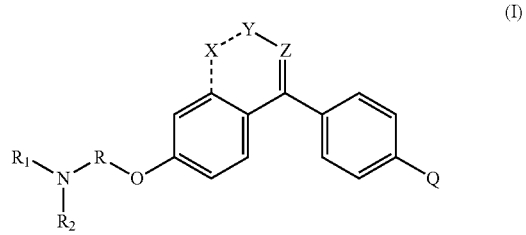

(I)

wherein Q may be, among other things, bromine, and $R_1$ and $R_2$ may be, among other things, aliphatic or aromatic groups. Formula I is disclosed in more detail below; see also [3,4]. Examples of analogues having an aromatic linker between the bromophenyl ring and the methoxyphenyl ring, or having a ketonic linker between the rings, are further given below:

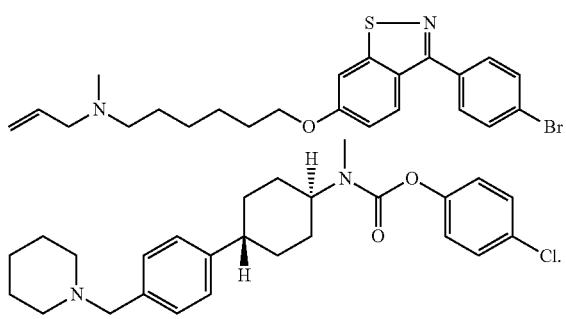

Among them, Ro 48-8071 (4'-[6-(Allylmethylamino)hexyloxy]-4-bromo-2'-fluorobenzophenone fumarate) illustrated below is a potent inhibitor of OSC.

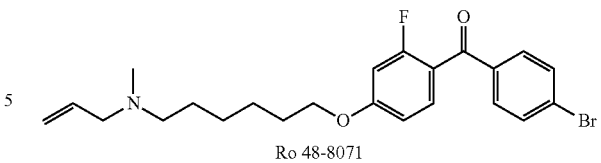

Ro 48-8071

Ro 48-8071, also known as (4-bromophenyl)[2-fluoro-4-[[6-(methyl-2-propenylamino)hexyl]oxy]phenyl]-methanone, is commercially available; see, e.g., Sigma-Aldrich, Product No. R2278. Although OSC, along with its inhibitors, has been studied as a target to reduce plasma cholesterol levels.[5] OSC has not previously been identified as a potential antitumor target.

p53 Tumor Suppressor.

Mutation of the p53 tumor suppressor gene is a common event in many types of tumors, such as breast cancers.[6-8] Mutant p53 (mtp53) protein is thought to promote tumor cell survival and resistance to chemotherapeutic drugs. Therefore, restoring p53 function by converting existing mtp53 to the wild-type p53 (wtp53) conformation is being pursued as one strategy to promote apoptosis of tumor cells, in susceptible cancers.

PRIMA-1.

The small molecule PRIMA-1 (p53 reactivation and induction massive apoptosis, also known as 2,2-bis(hydroxymethyl)-3-quinuclidinone, shown below) that was found from high-throughput experiments has gained considerable interest due to its ability to activate mutant p53 protein, thereby restoring the tumor suppressor function associated with wild-type p53.[9]

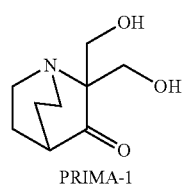

PRIMA-1

This effect has been demonstrated in vitro and in vivo, and shown to trigger massive apoptosis in human breast cancer cells.[10,11] While PRIMA-1's antitumor effects establish its importance as a potential agent against cancer, the mechanism of its reactivation of mutant p53 remains elusive. It is not certain whether it directly associates with p53, whereas some unpublished NMR experiments suggest against direct association. Thus, it is necessary to identify a direct protein target(s) of PRIMA-1, which may lead to new cancer treatment paradigms. Our results suggest that one of the protein targets for the chemotherapeutic effects of PRIMA-1 is the enzyme OSC.

Therefore, there is a need for establishing a new target for anticancer therapeutics, whereas the enzyme OSC and its signaling pathways serve as potential selective antitumor targets. There is also a need for identifying new inhibitors with potential therapeutic application in treatment of cancer by inhibiting the activity of OSC.

In one aspect, provided herein is a method for cancer therapy and treatment by targeting proteins, such as the enzyme oxidosqualene cyclase ('OSC'), in cholesterol biosynthetic pathway. In certain embodiments is provided a method of treatment of cancer comprising inhibiting an enzyme in the cholesterol biosynthetic pathway. In certain embodiments, the enzyme is OSC. In certain embodiments, the method comprises the step of inhibiting the activity of OSC in a cancer cell. The cancer cells can be of different types and/or origins, such as the cells are chosen from breast, prostate, lung, colon, ovary, pancreatic, liver, thyroid, stomach, uterine, lymphoma, brain, skin, kidney, mouth, throat, tongue, nasal, esophageal, and bladder cancer cells, as well as leukemia cells, and the drug resistant phenotypes thereof, as demonstrated in in vitro cancer cell growth experiments of nineteen cell lines with $IC_{50}$ analysis. In certain embodiments, a series of OSC inhibitors, i.e., the inhibitors containing a tertiary amine linked with aromatic ring structure, is used as the therapeutic agent in the cancer therapy. The compound 4'-[6-(allylmethylamino)hexyloxy]-4-bromo-2'-fluorobenzophenone fumarate (Ro 48-8071) is an exemplary inhibitor.

BRIEF DESCRIPTION OF THE DRAWINGS

FIG. 8 shows the effects of RO 48-8071 on pancreatic cancer cell lines Capan-1 (see FIG. 8A, left) and BxPC-3 (see FIG. 8B, right) viability over 24 and 48 hours.

Disclosed herein is a new and improved method for cancer therapy and treatment by targeting protein targets, such as the enzyme oxidosqualene cyclase ('OSC'), in cholesterol biosynthetic pathway. Also disclosed is the use of a compound which inhibits the activity of protein target in the cholesterol biosynthetic pathway of a cell for the treatment of cancer. Further disclosed is the use in the manufacture of a medicament which comprises a compound which inhibits the activity of protein target in the cholesterol biosynthetic pathway of a cell, for the treatment of cancer.

In certain embodiments, the method for cancer therapy and treatment involves reducing cancer cell viability via the step of inhibiting the activity of OSC in a cell. The method is applicable to cancer cells with various types and origins, such as, without limitation: breast, prostate, lung, colon, ovary, pancreatic, liver, thyroid, stomach, uterine, lymphoma, brain, skin, kidney, mouth, throat, tongue, nasal, esophageal, and bladder cancer cells, as well as leukemia cells, and the drug resistant phenotypes thereof.

In certain embodiments is provided a method of treatment of cancer comprising administering an inhibitor of an enzyme in the cholesterol biosynthetic pathway to a patient in need. In further embodiments, the enzyme in the cholesterol biosynthetic pathway is not HMG-CoA reductase. While inhibition of HMG-CoA reductase might be a viable method of treatment of cancer, it has been associated with toxicological side effects which limit its practical use.[19] In certain embodiments is provided a method of treatment of cancer comprising administering an OSC inhibitor to a patient in need. In certain embodiments is provided a method of treatment of cancer comprising administering Ro 48-8071 to a patient in need.

Also provided is a method of treatment of cancers that are notoriously known to be difficult to treat due to drug-resistance comprising inhibiting an enzyme in the cholesterol biosynthetic pathway. Therefore, in certain embodiments, the cancer to be treated is a drug-resistant cancer. In certain embodiments, the enzyme is OSC. In further embodiments is provided a method of treatment of a drug-resistant cancer comprising the administration of an OSC inhibitor. In further embodiments, the OSC inhibitor is Ro 48-8071. In further embodiments, the drug-resistant cancer is lung cancer or ovarian cancer. The efficacy of the method in the treatment of drug-resistant cancer is demonstrated by the effect of an OSC inhibitor (Ro 48-8071) on lung cancer H69AR and ovarian cancer OVCAR-3 cells in Table 2 below.

Figure 11A:
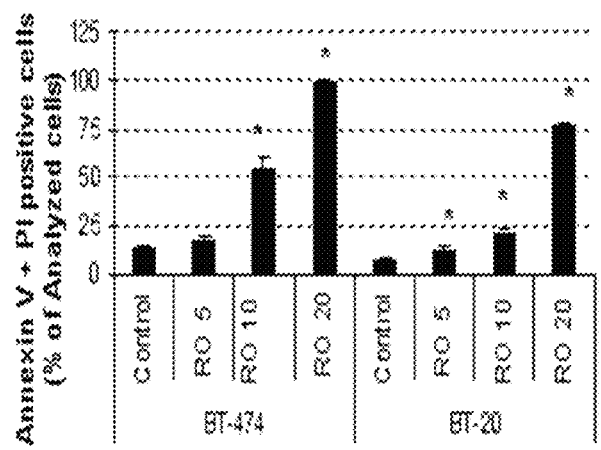
FIG. 11 depicts bar graphs from representative experiments showing annexin V positive plus PI positive cells (total dead cells) from BT-474, MCF-7, BT-20, and MDA-231 tumor cell lines. Dose proportional responses were seen in all cell lines.
Figure 11B:
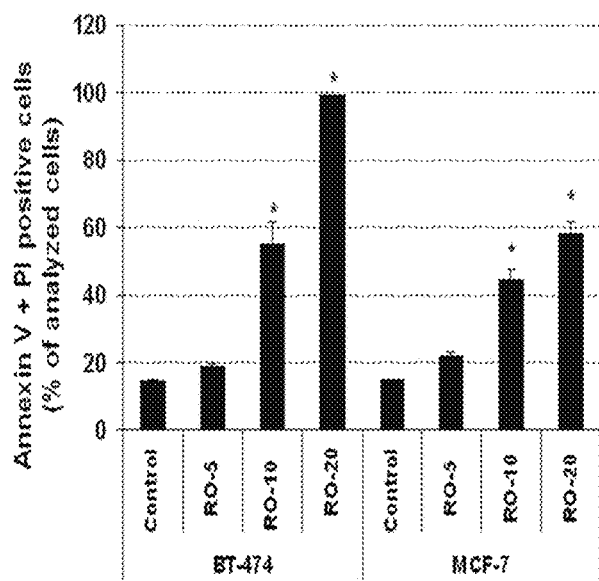
Figure 11C:
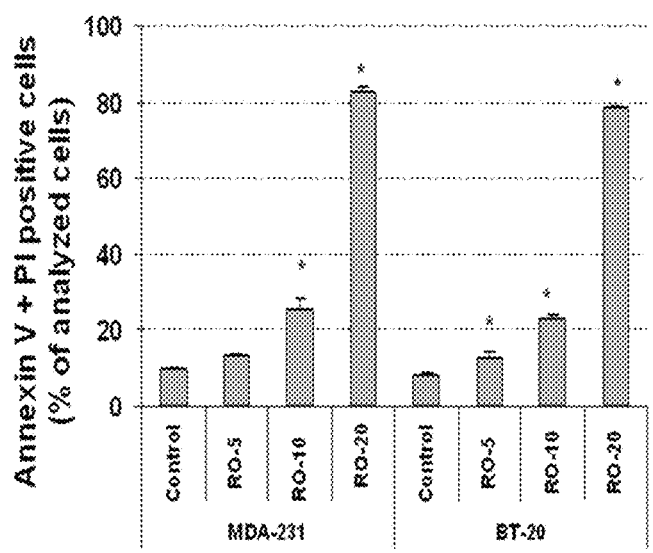
Figure 12A:
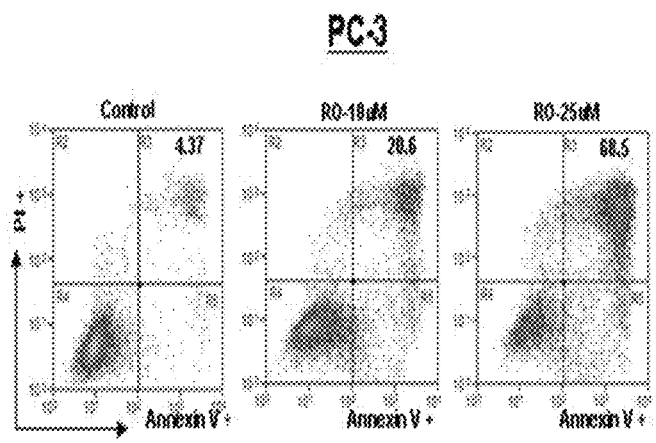
FIG. 12 shows the results of an apoptosis assay in androgen receptor negative human prostate cancer cells. PC-3 (FIG. 12A) and DU-145 (FIG. 12B) cells were treated with Ro 48-8071 and stained for early apoptosis (annexin V) and late apoptosis/necrosis (propidium iodide) markers; quadrant R5 shows annexin V positive cells and quadrant R3 shows annexin V plus propidium iodide positive cells. The percentages of apoptotic and dead cells (annexin V positive plus PI positive cells) from representative experiments are given in FIG. 12C.
Figure 12B:
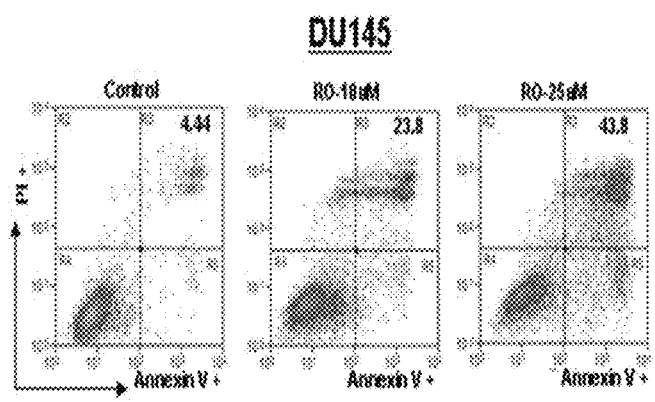
Figure 12C:
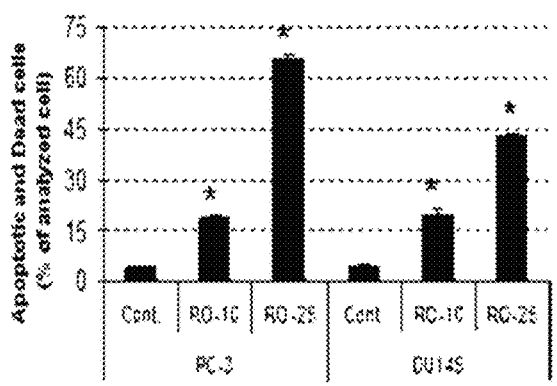

Also provided is a method of inducing cancer cell apoptosis and programmed cell death comprising inhibiting an enzyme in the cholesterol biosynthetic pathway. In certain embodiments, the enzyme is OSC. In further embodiments, the OSC inhibitor is Ro 48-8071. The efficacy of the method in inducing apoptosis is demonstrated by the effect of an OSC inhibitor (Ro 48-8071) on four breast and two prostate cancer cell lines in, e.g., Table 2, FIGS. 10, 11, and 12 below.

Figure 13A:
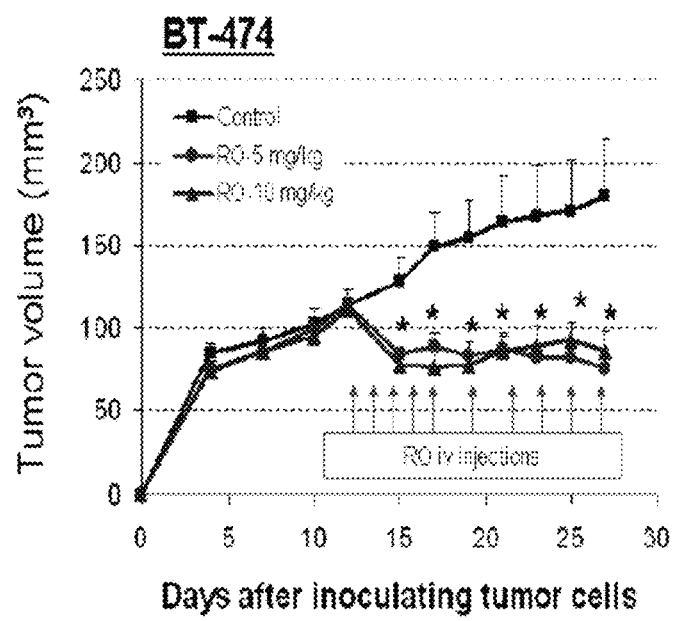
FIG. 13A shows RO 48-8071 suppressing the growth of xenograft breast tumor (BT-474) in vivo.

Also provided is a method of inhibiting tumor growth comprising inhibiting an enzyme in the cholesterol biosynthetic pathway. In certain embodiments, the enzyme is OSC. In further embodiments, the OSC inhibitor is Ro 48-8071. The efficacy of the method in inhibiting human breast and prostate tumor growth is demonstrated by the effect of an OSC inhibitor (Ro 48-8071) on human breast and prostate xenograft tumor growth in nude mice. See, e.g., FIGS. 13 and 14.

Also provided is a more effective anticancer agent than PRIMA-1. PRIMA-1 works only on mutant p53 cancer cell lines, but Ro 48-8071 works on both mutant and wild-type p53 cancer cell lines. Accordingly, provided herein is a method of treating cancer in both p53 mutated and non-p53 mutated cells comprising the administration of compound which inhibits an enzyme in the cholesterol biosynthesis pathway, wherein the compound is not PRIMA-1. In further embodiments, the enzyme in the cholesterol biosynthesis pathway is OSC. In further embodiments, the OSC inhibitor is Ro 48-8071. Additional OSC inhibitors are disclosed herein.

A class of compounds including a tertiary amine linked with aromatic ring structures, as new inhibitors for suppressing the viability of cancer cells is disclosed herein. In certain embodiments, new inhibitors have the Formula I:

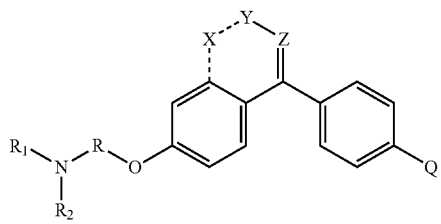

(I)

or a salt thereof, wherein:
X is chosen from hydrogen, halogen, O, $NR_3R_4$, S, $CH_2$, and CH;
Y is chosen from null, a bond, O and CH;
Z is chosen from O, N, and CH;
dashed bonds may be present or absent; if present, the bond may be single or double as valency allows;
R, $R_1$ and $R_2$ are independently chosen from alkyl, alkene, aryl, alkyne, cycloalkyl, and alkylcycloalkylalkyl, any of which may be optionally substituted;
$R_3$ and $R_4$ are independently chosen from a bond, hydrogen, lower alkyl, lower alkene, lower alkyne, aryl, and cycloalkyl, any of which may be optionally substituted; and
Q is chosen from bromine, chlorine and fluorine.
In certain embodiments, X is $NH_2$.
In certain embodiments, X is fluorine.
In certain embodiments, R is alkyl.
In certain embodiments, $R_1$ and $R_2$ are lower alkyl.
In further embodiments, new inhibitors have the Formula II:

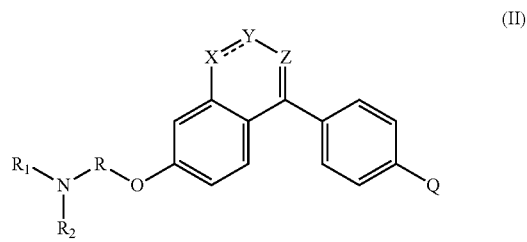

(II)

or a salt thereof, wherein:
X is chosen from O, N, $NR_3$, S, and CH;
Y is chosen from null, a bond, O and CH;
Z is chosen from O, N, and CH; and
the dashed bond may be present or absent;
R, $R_1$, and $R_2$ are independently chosen from alkyl, alkene, aryl, alkyne, cycloalkyl, and alkylcycloalkylalkyl, any of which may be optionally substituted;
$R_3$ is chosen from a bond, hydrogen, lower alkyl, lower alkene, lower alkyne, aryl, and cycloalkyl, any of which may be optionally substituted; and
Q is chosen from bromine, chlorine and fluorine.
In certain embodiments, R is alkyl.
In certain embodiments, $R_1$ and $R_2$ are lower alkyl.
In further embodiments, new inhibitors have the Formula III:

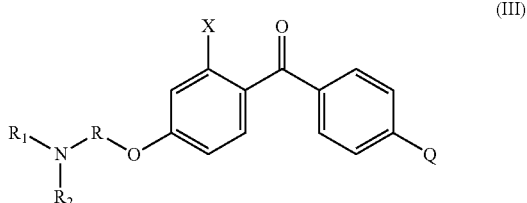

(III)

or a salt thereof, wherein:
X is chosen from hydrogen, halogen, and $NR_3R_4$;
R, $R_1$, and $R_2$ are independently chosen from alkyl, alkene, aryl, alkyne, cycloalkyl, and alkylcycloalkylalkyl, any of which may be optionally substituted;
$R_3$ and $R_4$ are independently chosen from a bond, hydrogen, lower alkyl, lower alkene, lower alkyne, aryl, and cycloalkyl, any of which may be optionally substituted; and
Q is chosen from bromine, chlorine and fluorine.
In certain embodiments, X is $NH_2$.
In certain embodiments, X is fluorine.

Provided herein, therefore, is a method of treating cancer comprising the step of administering to a patient in need thereof a therapeutically effective amount of an inhibitor of a protein target in the cholesterol biosynthetic pathway.

In certain embodiments, the protein target is not HMG-CoA reductase.

In certain embodiments, the protein target is oxidosqualene cyclase.

In certain embodiments, the cancer is chosen from cancers of the breast, prostate, lung, colon, ovary, pancreas, liver, thyroid, stomach, uterine, lymphoma, brain, skin, kidney, mouth, throat, tongue, nose, esophagus, and bladder, as well as leukemia, and the drug resistant phenotypes thereof.

In certain embodiments, the cancer cells do not have a p53 mutation.

In certain embodiments, the cancer cells are breast cancer cells which are HER2/neu positive.

In certain embodiments, the cancer cells are breast cancer cells which are estrogen receptor and progesterone receptor positive.

In certain embodiments, the cancer cells are breast cancer cells which are triple negative for estrogen receptor, progesterone receptor, and HER2/neu.

In certain embodiments, the cancer cells undergo apoptosis.

In certain embodiments, the inhibitor is a compound that is not PRIMA-1.

In certain embodiments, the compound is a tertiary amine linked to at least two aromatic ring structures.

In certain embodiments, the compound has Formula I, disclosed above, or an embodiment thereof.

In certain embodiments, the compound has Formula II, disclosed above, or an embodiment thereof.

In certain embodiments, the compound has Formula III, disclosed above, or an embodiment thereof.

In certain embodiments, the compound is 4'-[6-(allylmethylamino)hexyloxy]-4-bromo-2'-fluorobenzophenone fumarate.

Also provided herein is a method of reducing cancer cell viability comprising the step of inhibiting the activity of a protein target in cholesterol biosynthetic pathway of a cell.

In certain embodiments, the protein target is not HMG-CoA reductase.

In certain embodiments, the protein target is oxidosqualene cyclase.

In certain embodiments, the cells are chosen from breast, prostate, lung, colon, ovary, pancreatic, liver, thyroid, stomach, uterine, lymphoma, brain, skin, kidney, mouth, throat, tongue, nasal, esophageal, and bladder cancer cells, as well as leukemia cells, and the drug resistant phenotypes thereof.

In certain embodiments, the cells do not have a p53 mutation.

In certain embodiments, the cancer cells undergo apoptosis.

In certain embodiments, the cancer cells are breast cancer cells which are HER2/neu positive.

In certain embodiments, the cancer cells are breast cancer cells which are estrogen receptor and progesterone receptor positive.

In certain embodiments, the cancer cells are breast cancer cells which are triple negative for estrogen receptor, progesterone receptor, and HER2/neu.

In certain embodiments, the step of inhibiting is accomplished with a compound that is not PRIMA-1.

In certain embodiments, the compound is a tertiary amine linked to at least two aromatic ring structures.

In certain embodiments, the compound has Formula I, disclosed above, or an embodiment thereof.

In certain embodiments, the compound has Formula II, disclosed above, or an embodiment thereof.

In certain embodiments, the compound has Formula III, disclosed above, or an embodiment thereof.

In certain embodiments, the compound is 4'-[6-(Allylmethylamino)hexyloxy]-4-bromo-2'-fluorobenzophenone fumarate (Ro 48-8071).

Also provided herein is the use of a compound which inhibits the activity of protein targets in cholesterol biosynthetic pathway of a cell for the treatment of cancer.

In certain embodiments, the protein target is not HMG-CoA reductase.

In certain embodiments, the protein target is oxidosqualene cyclase.

In certain embodiments, the cancer is chosen from breast, prostate, lung, colon, ovary, pancreas, liver, thyroid, stomach, uterine, lymphoma, brain, skin, kidney, mouth, throat, tongue, nasal, esophageal, and bladder cancer, as well as leukemia, and a drug resistant phenotype thereof.

In certain embodiments, the cells do not have a p53 mutation.

In certain embodiments, the cancer cells undergo apoptosis.

In certain embodiments, the cancer is breast cancer, the cells of which are HER2/neu positive.

In certain embodiments, the cancer is breast cancer, the cells of which are estrogen receptor and progesterone receptor positive.

In certain embodiments, the cancer is breast cancer, the cells of which are triple negative for estrogen receptor, progesterone receptor, and HER2/neu.

In certain embodiments, step of inhibiting is accomplished with a compound that is not PRIMA-1.

In certain embodiments, the compound is a tertiary amine linked to at least two aromatic ring structures.

In certain embodiments, the compound has Formula I, disclosed above, or an embodiment thereof.

In certain embodiments, the compound has Formula II, disclosed above, or an embodiment thereof.

In certain embodiments, the compound has Formula III, disclosed above, or an embodiment thereof.

In certain embodiments, the compound is 4'-[6-(Allylmethylamino)hexyloxy]-4-bromo-2'-fluorobenzophenone fumarate (Ro 48-8071).

Also provided herein is a method for determining the intracellular activity of OSC comprising:
  a) providing a sample of mammalian cancer cells to be tested for OSC activity, and
  b) determining the level of conversion of 2,3-(S)-oxidosqualene to lanosterol in the sample,
wherein the level of either 2,3-(S)-oxidosqualene or lanosterol correlates with the level of intracellular OSC activity.

Also provided herein is a method for determining the pro-apoptotic or anti-proliferative properties of a compound comprising:
  a) contacting a sample of mammalian cancer cells comprising OSC activity with the compound;
  b) measuring the level of any one or more of
    i) a marker of apoptosis and
    ii) one or more of 2,3-(S)-oxidosqualene, lanosterol, and cholesterol in the sample; and
  c) comparing the levels of any one or more of (i) and (ii) in the sample contacted with the compound with the levels of any one or more of (i) and (ii) in a control sample, wherein the levels of the 2,3-(S)-oxidosqualene and the marker of apoptosis correlate directly with the level of apoptosis and anti-proliferation, and the levels of the lanosterol and cholesterol correlate inversely with the level of apoptosis and anti-proliferation.

In certain embodiments, the method measures the level of any one of 2,3-(S)-oxidosqualene, lanosterol, and cholesterol in the sample.

In certain embodiments, the method measures the level of a marker of apoptosis in the sample the marker of apoptosis is chosen from annexin V and Caspase 3.

Also provided herein is a method for identifying an agent that inhibits the proliferation of cancer cells, comprising:
 a) providing a test sample of cancer cells comprising OSC activity;
 b) either:
  i) determining the activity of OSC in the test sample by contacting the sample with a test agent and comparing the level of any one of 2,3-(S)-oxidosqualene, lanosterol, and cholesterol in the test sample with the level of any one of 2,3-(S)-oxidosqualene, lanosterol, and cholesterol in a control sample; or
  ii) determining the activity of OSC in the test sample by measuring the level of any one of 2,3-(S)-oxidosqualene, lanosterol, and cholesterol in the sample at a first time point, contacting the sample with a test agent, and measuring the level of any one of 2,3-(S)-oxidosqualene, lanosterol, and cholesterol in the sample at a second time point; and
 c) determining whether the test agent is an agent that modulates the intracellular activity of OSC based on either:
  i) a change in level of any one of 2,3-(S)-oxidosqualene, lanosterol, and cholesterol in the test sample compared to the control sample; or
  ii) a change in level of any one of 2,3-(S)-oxidosqualene, lanosterol, and cholesterol in the test sample from the first time point to the second time point;
wherein the level of any one of 2,3-(S)-oxidosqualene, lanosterol, and cholesterol correlates with the level of intracellular OSC activity.

Also provided herein is a method for identifying an agent that modulates the intracellular activity of OSC comprising:
 a) providing a test sample of cancer cells comprising OSC activity;
 b) either:
  i) determining the activity of OSC in the test sample by contacting the sample with a test agent and comparing the level of cancer cell viability in the test sample with the level of cancer cell viability in a control sample; or
  ii) determining the activity of OSC in the test sample by measuring the level of viable cancer cells in the sample at a first time point, contacting the sample with a test agent, and measuring the level of viable cancer cells in the sample at a second time point; and
 c) determining whether the test agent is an agent that modulates the intracellular activity of OSC based on either:
  i) a change in level of viable cancer cells in the test sample compared to the control sample; or
  ii) a change in level of any viable cancer cells in the test sample from the first time point to the second time point;
wherein the level of viable cancer cells correlates with the level of intracellular OSC activity.

Also provided herein is a method of screening a plurality of chemical compounds to identify a compound which inhibits OSC activity, comprising:
 a) contacting a test sample of cancer cells comprising OSC activity with the plurality of compounds not known to inhibit OSC activity;
 b) determining the level of any one of 2,3-(S)-oxidosqualene, lanosterol, and cholesterol in the test sample; wherein the level of any one of 2,3-(S)-oxidosqualene, lanosterol, and cholesterol correlates with the level of intracellular OSC activity;
 c) comparing the intracellular activity of OSC in the test sample with that in a control sample; and
 d) where inhibition of OSC activity by the plurality of compounds is observed, separately determining the inhibition of OSC activity of each compound included in the plurality of compounds, so as to thereby identify any individual compound included therein which inhibits OSC.

Also provided herein is a method of preparing a composition comprising a chemical compound which inhibits OSC activity, comprising:
 a) providing a test sample of cancer cells comprising OSC activity;
 b) contacting the test sample with a test compound;
 c) determining the degree of reduction of OSC activity in the test sample compared to a control sample, or at a test time point compared to a control time point, to determine the degree of inhibition of activity of OSC in the test sample, wherein the level of
  i) any of 2,3-(S)-oxidosqualene, lanosterol, and cholesterol;
  ii) a marker of apoptosis; or
  iii) viable cancer cells
  directly correlates with the level of OSC activity;
 d) identifying the test compound as a compound that inhibits the activity of OSC, and admixing the test compound so identified, or a functional analog or homolog of the test compound, with a carrier, thereby preparing the composition.

In certain embodiments, the level of any one of 2,3-(S)-oxidosqualene, lanosterol, and cholesterol directly correlates with the level of OSC activity.

In certain embodiments, the marker of apoptosis directly correlates with the level of OSC activity, and the marker of apoptosis is chosen from annexin V and Caspase 3.

Also provided herein is a method for identifying a compound for the treatment of cancer comprising:
 a) providing a test sample of cancer cells;
 b) contacting the test sample with a test compound;
 c) determining the degree of reduction of any one or more of 2,3-(S)-oxidosqualene, lanosterol, and cholesterol;
 d) optionally, determining:
  i) the increase in the level of a marker of apoptosis; and
  ii) the decrease in the level of viable cancer cells;
 e) identifying the test compound as a compound that
  i) inhibits the activity of an enzyme in the cholesterol biosynthetic pathway;
  ii) promotes apoptosis in cancer cells; or
  iii) kills cancer cells; and
wherein the level of any one of 2,3-(S)-oxidosqualene, lanosterol, and cholesterol correlates with the level of anticancer activity, such that a lesser reduction in the amount of 2,3-(S)-oxidosqualene in the test sample compared to the control sample indicates greater anticancer activity; and a greater reduction in the level of lanosterol or cholesterol compared to the control sample indicates greater anticancer activity.

Also provided herein is a method of preparing a composition comprising a compound for the treatment of cancer, comprising:
 a) providing a test sample of cancer cells;
 b) contacting the test sample with a test compound;
 c) determining the degree of reduction of any of 2,3-(S)-oxidosqualene, lanosterol, and cholesterol;
 d) optionally, determining:
  i) the increase in the level of a marker of apoptosis; and
  ii) the decrease in the level of viable cancer cells;
 e) identifying the test compound as a compound that
  i) inhibits the activity of an enzyme in the cholesterol biosynthetic pathway;
  ii) promotes apoptosis in cancer cells; or
  iii) kills cancer cells; and
 f) admixing the test compound so identified, or a functional analog or homolog of the test compound, with a carrier, thereby preparing the composition.

In certain embodiments, the enzyme in the cholesterol biosynthetic pathway is not HMG-CoA reductase.

In certain embodiments, the enzyme in the cholesterol biosynthetic pathway is OSC.

In certain embodiments, the marker of apoptosis is chosen from annexin V and Caspase 3.

Also provided herein is a method of screening for an agent that inhibits tumor growth in a mammal, said method comprising:
 a) contacting a cell with a test agent;
 b) detecting the activity of OSC;
 c) scoring a decrease in OSC activity, as compared to the activity of OSC in a control, as an indication that said test agent is an agent that inhibits tumor growth in a mammal.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position. When a ring or chain element is designated to be a bond, what is meant is that the flanking moieties have a covalent bond between them. For example, in the chain X—Y—Z, when Y is a bond, the chain collapses to X—Z.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "halo," or "halogen," as used herein, alone or in combination, refers to fluorine, chlorine, bromine, or iodine.

The term "lower," as used herein, alone or in a combination, where not otherwise specifically defined, means containing from 1 to and including 6 carbon atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, ester, acyl, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

As used herein, the term "modulate" means to increase or decrease the activity of a target or the amount of a substance.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

A "sample" as used herein refers to a biological material which can be tested, e.g., for the presence of OSC activity, or to determine if a test agent is capable of modulating the activity of OSC either in vitro, or inside a cell. Such samples may contain purified or semi-purified, or non purified preparations of OSC, for in vitro measurements. Samples may also comprise cells comprising intracellular OSC, for intracellular measurements of OSC activity. Samples of cells will typically contain buffers and salts to maintain physiological ionic strength and pH and be maintained at an appropriate temperature to preserve viability. Cells may be obtained from any source, including tissue culture, or tissue samples. In one aspect, such cells are mammalian cells. A sample may also include suitable control reagents (control samples).

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, polymorphs, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. Suitable acid addition salts include those formed with both organic and inorganic acids, and will normally be pharmaceutically acceptable. However, salts of non-pharmaceutically acceptable salts may be of utility in the preparation and purification of the compound in question. Basic addition salts may also be formed and be pharmaceutically acceptable. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium (e.g., NaOH), potassium (e.g., KOH), calcium (including Ca(OH)$_2$), magnesium (including Mg(OH)$_2$ and magnesium acetate), zinc, (including Zn(OH)$_2$ and zinc acetate) and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

While it may be possible for the compounds and prodrugs disclosed herein to be administered as the raw chemical, it is also possible to present them as a pharmaceutical formulation. Accordingly, provided herein are pharmaceutical formulations which comprise one or more of certain compounds and prodrugs disclosed herein, or one or more pharmaceutically acceptable salts, esters, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds and prodrugs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and prodrugs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds and prodrugs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds and prodrugs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and prodrugs to allow for the preparation of highly concentrated solutions.

In addition to the formulations described previously, a compound or prodrug as disclosed herein may also be formulated as a depot preparation. Such long acting formulations may be administered by implantation (for example subcutaneously or intramuscularly) or by intramuscular injection. Thus, for example, the compounds and prodrugs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds and prodrugs may also be formulated in rectal compositions such as suppositories or retention enemas, e.g., containing conventional suppository bases such as cocoa butter, polyethylene glycol, or other glycerides.

Certain compounds and prodrugs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds and prodrugs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds and prodrugs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, $2^{nd}$, J Neuroimmune Pharmacol. March 2007; 2(1):81-6. Epub 2006 Sep. 15.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds and prodrugs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compound or prodrug which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds and prodrugs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds and prodrugs described herein (or a pharmaceutically acceptable salt or ester thereof) in combination with another therapeutic agent. By way of example only, if one of the side effects experienced by a patient upon receiving one of the compounds herein for the treatment of actinide poisoning is depletion of essential trace minerals required by the body for proper functioning, then it may be appropriate to administer a strong chelating agent in combination with supplements of essential trace minerals required by the body for proper functioning, for example zinc and magnesium, to replace those which will inadvertently be lost to chelation therapy. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for thalassemia involving administration of one of the compounds described herein, increased therapeutic benefit may result by also providing the patient with another therapeutic agent for thalas semis, for example deferoxamine. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds disclosed herein with one or more agents chosen from: aromatase inhibitors, antiestrogens, anti-progestins, anti-androgens, or gonadorelin agonists, topoisomerase 1 and 2 inhibitors, microtubule active agents, alkylating agents, antineoplastic, antimetabolite, dacarbazine (DTIC), or platinum containing compound, lipid or protein kinase targeting agents, protein or lipid phosphatase targeting agents, anti-angiogenic agents, agents that induce cell differentiation, bradykinin 1 receptor and angiotensin II antagonists, cyclooxygenase inhibitors, heparanase inhibitors, lymphokines or cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, aminopeptidase inhibitors.

For the treatment of oncologic diseases and solid tumors, compounds disclosed herein may be administered with an agent selected from the group comprising: dacarbazine (DTIC), alkylating agents (e.g., melphalan) anthracyclines (e.g. doxorubicin), corticosteroids (e.g. dexamethasone), Akt inhibitor (e.g. Perifosine), aromatase inhibitors, antiestrogen, anti-androgen, or a gonadorelin agonists, topoisomerase land 2 inhibitors, microtubule active agents, alkylating agents (e.g. cyclophosphamide, temozolomide), antineoplastic antimetabolite, or platinum containing compounds, MITC, nitrosoureas, taxanes, lipid or protein kinase targeting agents, protein or lipid phosphatase targeting agents, anti-angiogenic agents, IMiDs (e.g. thalidomide, lenalidomide), protease inhibitors (e.g. bortezomib, NPI0052), IGF-1 inhibitors, CD40 antibody, Smac mimetics (e.g. telomestatin), FGF3 modulator (e.g. CHIR258), mTOR inhibitor (Rad 001), HDAC inhibitors (e.g. SAHA, Tubacin), IKK inhibitors, P38MAPK inhibitors, HSP90 inhibitor (e.g. 17-AAG), and other multikinase inhibitors (e.g. sorafenib).

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating disorders and symptoms relating to metal toxicity in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of disorders and symptoms relating to metal toxicity.

The compounds, compositions, and methods disclosed herein are useful for the treatment of cancer. Specific cancers to be treated by the compounds, compositions, and methods disclosed herein include cancers of the breast, prostate, lung, colon, ovary, pancreas, liver, thyroid, stomach, uterine, lymphoma, brain (including, e.g., neuroblastoma and gliobalstoma), skin, kidney, mouth, throat, tongue, and bladder, as well as leukemia. The cancer may be hormone-dependent or hormone-resistant, such as in the case of breast cancers. In certain embodiments, the cancer is a solid tumor. In certain embodiments, the cancer is and a drug resistant phenotype of a cancer disclosed herein or known in the art.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

Oxidosqualene Synthase as a Target for Cancer Therapy

As disclosed herein, a new anti-cancer target was identified through studies of PRIMA-1, a small molecule that activates mutant p53 protein and restores the tumor-suppressing functionality present in wild-type p53. A bioinformatics approach was applied and inverse protein-ligand docking performed to screen for protein targets of PRIMA-1 from an existing protein structure database. The docking software employed is the MDock software package written by the inventor.[12-16] The protein database employed is the Potential Drug Target Database (PDTD).[17] The proteins were ranked according to their energy scores (the lower the score, the higher the binding affinity) and then clustered. The top human protein target, the enzyme oxidosqualene cyclase ('OSC') was selected for assay.

Figure 1:
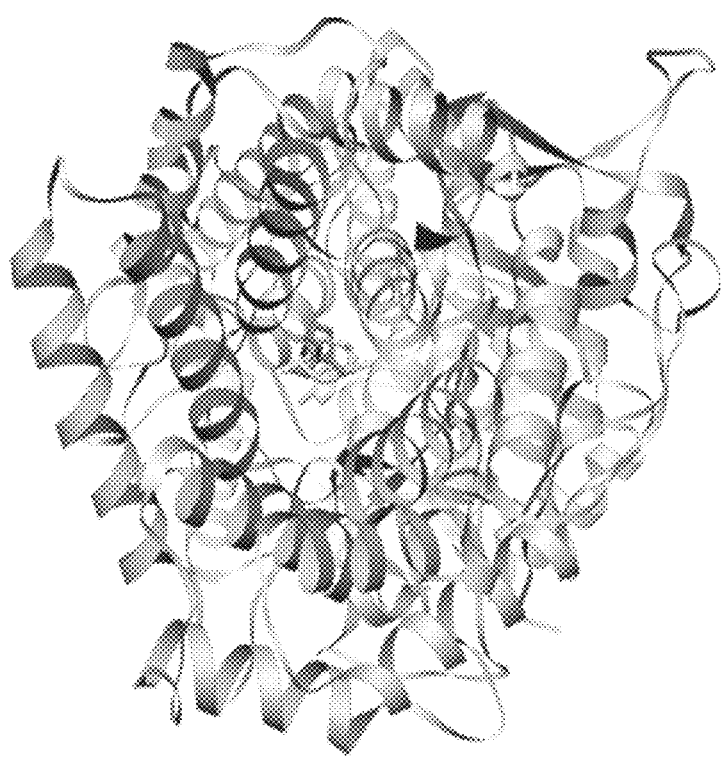
FIG. 1 is a ribbon depiction of oxidosqualene cyclase ('OSC') docked with PRIMA-1 (darker structure toward top of binding pocket as pictured) and the inhibitor, Ro 48-8071 (lighter structure).

An existing series of inhibitors of OSC were also investigated; the binding mode of the inhibitors docked into OSC was compared with that of PRIMA-1 docked into OSC. As the shown in FIG. 1, the docking configuration of Ro 48-8071 (4'-[6-(Allylmethylamino)hexyloxy]-4-bromo-2'-fluorobenzophenone fumarate) and PRIMA-1 with OSC partially overlap in the binding pocket.

Inhibitors of OSC

OSC inhibitors may be identified by methods known in the art. For example, microsomal assays employing human, rat, or other liver microsomes may be used, wherein the amount of radiolabeled 2,3-(S)-oxidosqualene consumed or lanosterol produced by microsomes treated with test compound measured and compared with control. Alternatively, whole cell assays may be used to measure cholesterol biosynthesis. For example, liver cells may be incubated with test compound and a radiolabeled cholesterol biosynthetic pathway substrate such as acetic acid or mevalonic acid, and the cholesterol produced (or perhaps the substrate consumed) may be measured according to methods known in the art and compared to control. Animal studies may also be used to measure, for example, liver or serum cholesterol in treated versus untreated subjects. See, e.g., WO199611201A1, WO199706802A1, and EP01346994.

Additional examples of OSC inhibitors are given below in Table 1.

TABLE 1

| Structure | OSC IC$_{50}$ (nM) |
|---|---|
| 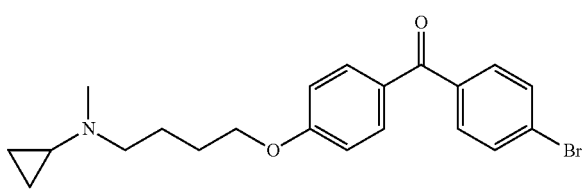 [SMILES: CN(CCCCOc1ccc(C(=O)c2ccc(Br)cc2)cc1)C1CC1] | 19 |

TABLE 1-continued

| Structure | OSC IC$_{50}$ (nM) |
| --- | --- |
| *[structure: allyl-N(Me)-CH2-CH=CH-CH2-O-benzofuran-3-yl-C6H4-Br]* | 500 (83.3) |
| *[structure: allyl-N(Me)-CH2-biphenyl-C(=O)-C6H4-Br]* | 16 |
| *[structure: cyclopropyl-N(Me)-(CH2)6-O-C6H3(F)-C(=O)-C6H4-Br]* | 98 |
| *[structure: allyl-N(Me)-CH2-CH=CH-CH2-O-C6H4-C(=O)-C6H4-Br]* | 3.0 |
| *[structure: allyl-N(Me)-CH2-CH=CH-CH2-O-benzisoxazol-3-yl-C6H4-Br]* | 29 |
| *[structure: cyclopropyl-N(Me)-CH2-cyclopropyl-CH2-O-C6H3(F)-C(=O)-C6H4-Br]* | 439 |
| *[structure: allyl-N(cyclopropyl)-CH2-cyclopropyl-CH2-O-C6H4-C(=O)-C6H4-Br]* | 223 |
| *[structure: allyl-N(Me)-(CH2)6-O-C6H3(F)-C(=O)-C6H4-Br]* | 6.5 |

TABLE 1-continued

| Structure | OSC IC$_{50}$ (nM) |
|---|---|
| 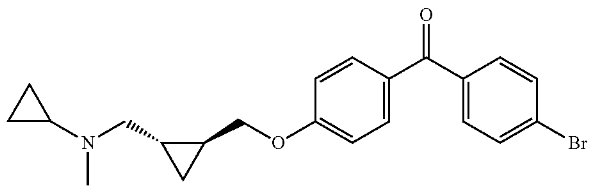 [SMILES: CN(C[C@H]1C[C@@H]1COc1ccc(C(=O)c2ccc(Br)cc2)cc1)C1CC1] | 22 |
| 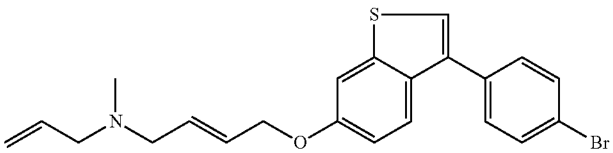 [SMILES: C=CCN(C)C/C=C/COc1ccc2c(-c3ccc(Br)cc3)csc2c1] | 13.5 |
| 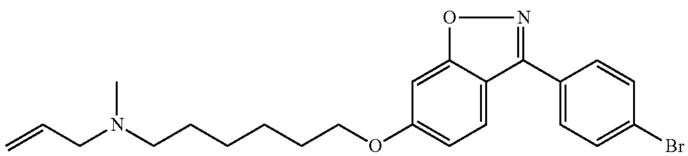 [SMILES: C=CCN(C)CCCCCCOc1ccc2c(-c3ccc(Br)cc3)noc2c1] | 380 (79.0) |
| 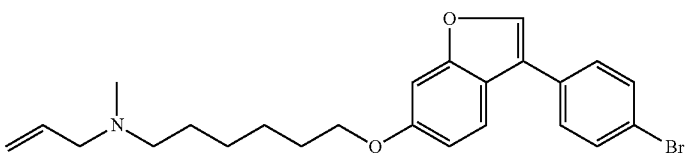 [SMILES: C=CCN(C)CCCCCCOc1ccc2c(-c3ccc(Br)cc3)coc2c1] | 610 (86.0) |
| 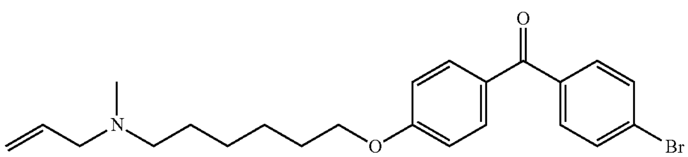 [SMILES: C=CCN(C)CCCCCCOc1ccc(C(=O)c2ccc(Br)cc2)cc1] | 5.4 |
| 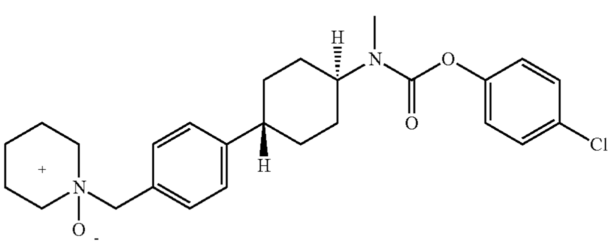 | 640 (86.5) |
| 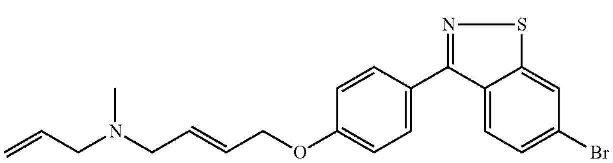 [SMILES: C=CCN(C)C/C=C/COc1ccc(-c2nsc3cc(Br)ccc23)cc1] | 1860 (94.9) |
| 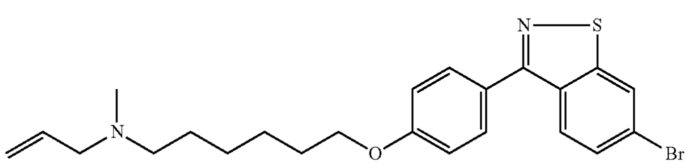 [SMILES: C=CCN(C)CCCCCCOc1ccc(-c2nsc3cc(Br)ccc23)cc1] | 1900 (95.0) |
| 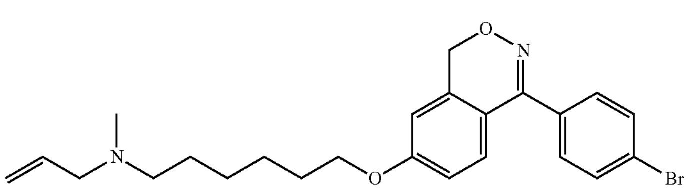 [SMILES: C=CCN(C)CCCCCCOc1ccc2c(c1)CON=C2c1ccc(Br)cc1] | 4.1 |

TABLE 1-continued
| Structure | OSC IC$_{50}$ (nM) |
|---|---|
| 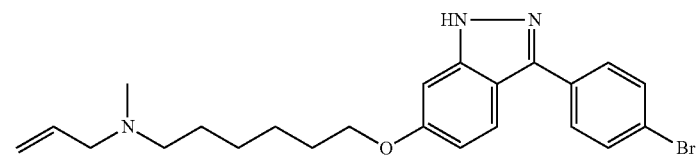 | 39 |
| 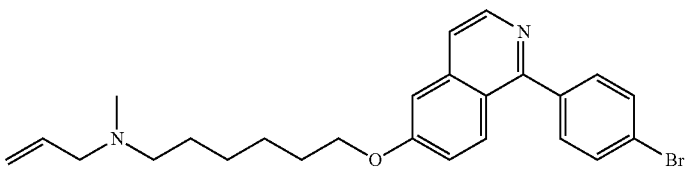 [SMILES: C=CCN(C)CCCCCCOc1ccc2c(-c3ccc(Br)cc3)nccc2c1] | 3.5 |
| 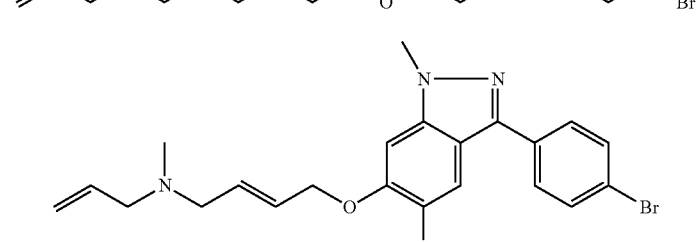 | 29 |
| 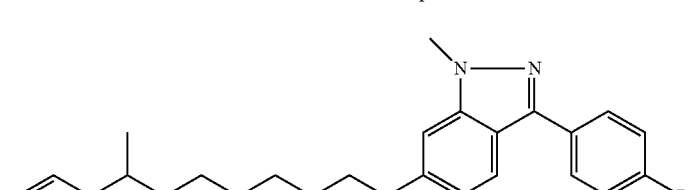 | 19.6 |
| 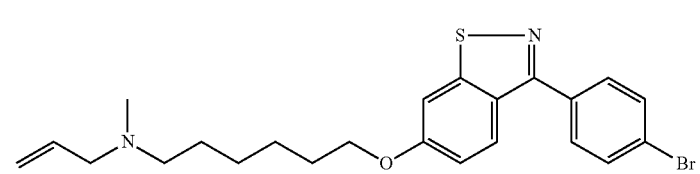 | 2.9 |
| 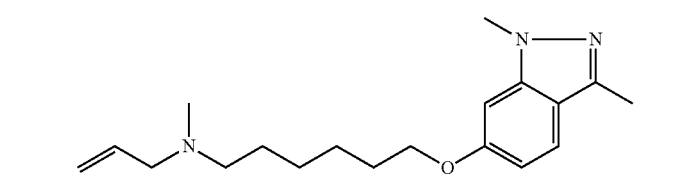 [SMILES: C=CCN(C)CCCCCCOc1ccc2c(C)nn(C)c2c1] | 240 (70.4) |
| 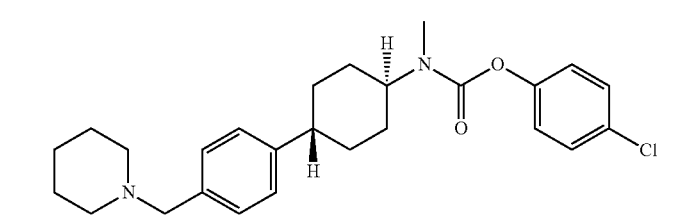 [SMILES: CN(C(=O)Oc1ccc(Cl)cc1)[C@H]1CC[C@H](c2ccc(CN3CCCCC3)cc2)CC1] | 11.3 |
| 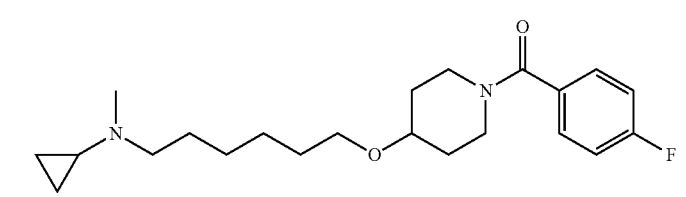 [SMILES: CN(CCCCCCOC1CCN(C(=O)c2ccc(F)cc2)CC1)C1CC1] | 48 |

TABLE 1-continued

| Structure | OSC IC$_{50}$ (nM) |
|---|---|
| 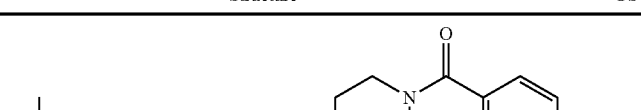 | 71 |
| 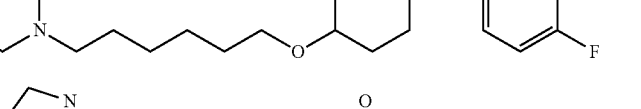 | 36 |

This table was adapted from Lenhart A et al., Binding Structures and Potencies of oxidosqualene cyclase inhibitors with the homologous squalene-hopene cyclase. *J. Med. Chem.* 2003, 46:2083-2092. One of the compounds above, Ro-48-8071, may be synthesized as described in [5], excerpts of which are provided below.

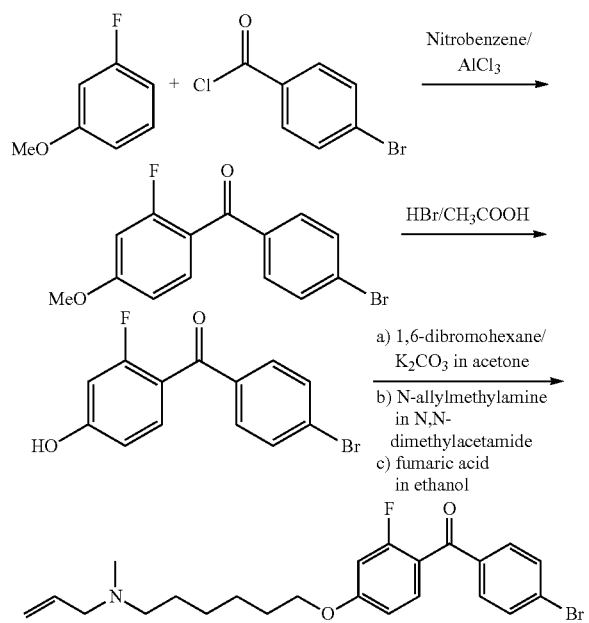

Ro 48-8071 (fumarate, MW=564.45) was synthesized as shown above. All intermediates and Ro 48-8071 were characterized by 250 MHz $^1$HNMR, IR, MS, and microanalyses. Melting points (uncorrected) were determined using a Büchi 510 apparatus. Proton NMR spectra were recorded on a Bruker AC250 spectrometer, and δ values are given in ppm relative to tetramethylsilane. IR spectra of KBr pellets were recorded using a Nicolet 7199-FT IR spectrometer. Mass spectra (MS) were obtained using the pneumatically assisted electrospray technique (Perkin-Elmer Sciex, type API-111). Results of elemental analyses were within 0.3% of theoretical values.

(4-Bromophenyl)-(2'-fluoro-4'-methoxyphenyl)-methanone [1]

Aluminum chloride (144 g, 1.08 mol) was added to 450 ml precooled nitrobenzene keeping the temperature <8° C. Then, a suspension of 219.5 g (1 mol) 4-bromobenzoyl chloride in 200 ml nitrobenzene was added over 20 min, followed 10 min later by 108.5 ml (0.95 mol) 3-fluoroanisole. The reaction mixture was warmed to room temperature overnight, mixed into iced water (1.51), and extracted with 3×11 dichloromethane. The three organic phases were washed sequentially with 2×11 water, pooled, and dried (Na$_2$SO$_4$). Evaporation (85° C., 1 Torr) provided a mixture of (4-bromophenyl)-(2-fluoro-4-methoxyphenyl)-methanone and (4-bromophenyl)-(4'-fluoro-2'-methoxyphenyl)-methanone which was immediately dissolved in 300 ml ethyl acetate, and crystallized at room temperature. The crystals were filtered off and washed with 100 ml ethyl acetate and 3×100 ml cyclohexane to give pure (4-bromophenyl)-(2'-fluoro-4'-methoxyphenyl)-methanone (122.4 g, 41.6%): mp 125-126° C.; IR 1643 cm$^{-1}$; $^1$HNMR (CDCl$_3$) δ 3.87 (s, OCH$_3$), 6.66 (dd, J=12.1, 2.4 Hz 1H, 3'-H) 6.80 (dd, J=8.7, 2.4 Hz, 1H, 5'-H), 7.54-7.68 (m, 5H, arom H); EIMS m/z 308 (M$^+$, 1 Br). Calculated analysis for C$_{14}$H$_{16}$OBrFO$_2$: C, 54.40; H, 3.26; F, 6.15; Br, 25.85. Found: C, 54.57; H, 3.35; F, 6.21; Br, 26.07.

(4-Bromophenyl)-(2'-fluoro-4'-hydroxyphenyl)-methanone [2]

A suspension of 61.8 g (200 mmol) of [1] in 400 ml acetic acid was treated with 230 ml 62%-aqueous hydrobromic acid, and stirred at 125° C. for 8 h prior to evaporation. The residue was dissolved in 500 ml ethyl acetate and washed with 300 ml saturated sodium bicarbonate and 300 ml 10%-sodium chloride solution. The aqueous phases were extracted with 2×500 ml ethyl acetate. The organic phase was dried (Na$_2$SO$_4$) and evaporated to give orange crystals of (4-bromophenyl)-(2'-fluoro-4'-hydroxyphenyl)-methanone [2] (57.2 g, 96.9%): mp 62-63° C.; IR 1652 cm$^{-1}$; $^1$HNMR (DMSO-6.66 (dd, J=12.1, 2.4 Hz 1H, 3'-H), 6.80 (dd, J=8.7, dtj) a 6.68 (dd, J=12.6, 2.2 Hz, 1H, 3'-H), 6.77 (dd, J=8.5, 2.2 Hz, 1H, 5'-H), 7.49 (dd, J=8.5, 8.5 Hz, 1H, 6'-H), 7.64 and 7.75 (AA'BB', 4H, 2,3,5,6-H), 10.85 (br s, 1H, OH); EIMS m/z 294 (M$^+$, 1Br). Calculated analysis for C$_{13}$H$_8$BrFO$_2$: C, 52.91; H, 2.73; F, 6.44; Br, 27.08. Found: C, 52.94; H, 2.74; F, 6.42; Br, 26.84.

[4'-(6-Allyl-methyl-amino-hexyloxy)-2'-fluorophenyl]-(4-bromophenyl)-methanone fumarate [3]

A mixture of 35.4 g (120 mmol) [2], 54.9 ml (360 mmol) 1,6-dibromohexane and 49.8 g (360 mmol) potassium carbonate in 1100 ml acetone was vigorously stirred at 75° C.

for 5 h. After filtration and evaporation, the residue was dissolved in dichloromethane treated with sodium sulfate, filtered again, and evaporated. Crystallization with 400 ml cyclohexane-hexane 1:3 (v/v) first at 0° C. and then at −78° C. gave 53.2 g (116 mmol) crude [4'-(6-bromo-hexyloxy)-2'-fluorophenyl]-(4-bromophenyl)-methanone. This product was dissolved in 390 ml N,N-dimethylacetamide, cooled to 0° C., and 22.5 ml (232 mmol) N-allylmethylamine was added dropwise. After 22 h at room temperature the reaction was cooled to 0° C., and treated again with 22.5 ml (232 mmol) N-allylmethylamine. After 5 h the solution was evaporated (70° C., 1 Torr), neutralized with 300 ml saturated sodium bicarbonate, and extracted with 3×400 ml dichloromethane. The organic phase was dried ($Na_2SO_4$) evaporated to dryness, and purified by flash column chromatography (silica gel 0.04-0.063 mm, dichloromethane-methanol 95:5 (v/v), producing 37.7 g (84.1 mmol) of [4'-(6-allylmethyl-amino-hexyloxy)-2'-fluorophenyl]-(4-bromophenyl)-methanone. The free amine and 8.8 g (75.7 mmol) of fumaric acid were dissolved in 200 ml ethanol, evaporated, and crystallized from acetone-ethylacetate-ether to give [4'-(6-allylmethyl-amino-hexyloxy)-2'-fluoro-phenyl]-(4-bromophenyl)-methanone fumarate [3] (36.2 g, 53.4%): mp 86-88° C.; IR 1653 cm$^{-1}$; $^1$HNMR (DMSO-$_{d6}$) δ 1.25-1.60 (m, 6H, OCH$_2$CH$_2$CH$_2$CH$_2$CH$_2$CH$_2$N), 1.70-1.80 (m, 2H, OCH$_2$CH$_2$CH$_2$CH$_2$CH$_2$CH$_2$N), 2.24 (s, 3H, NCH$_3$), 2.40-2.50 (m, 2H, OCH$_2$CH$_2$CH$_2$CH$_2$CH$_2$CH$_2$N), 3.11 (d, J=6.5 Hz, 2H, NCH$_2$CHCH$_2$), 4.08 (t, J=6.4 Hz, 2H, OCH$_2$CH$_2$CH$_2$CH$_2$CH$_2$CH$_2$N), 5.17-5.27 (m, 2H, NCH$_2$CHCH$_2$), 5.75-5.90 (m, 1H, NCH$_2$CHCH$_2$), 6.67 (s, 2H, fumarate), 6.91-7.00 (m, 2H, 3',5'-H), 7.56 (dd, J=8.6, 8.6 Hz, 1H, 6'-H), 7.65 and 7.76 (AA'BB', 4H, 2,3,5,6-H); EIMS m/z 448 (M$^+$, 1Br). Calculated analysis for $C_{23}H_{27}NBrFO_2 \cdot C_4H_4O_4$; C, 57.45; H, 5.54; N, 2.48; F, 3.37; Br, 14.16. Found: C, 57.39; H, 5.57; N, 2.50; F, 3.38; Br, 14.15.

Additional examples of OSC inhibitors are given below. One such inhibitor is, U18666A (also known as 3-beta-(2-(diethylamino)ethoxy)androst-5-en-17-one), shown below:

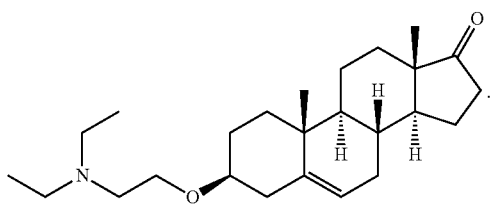

Although U18666A is a potent inhibitor of OSC, its therapeutic use may be limited by possible toxicological effects including cataract formation. [20]

Yet additional examples of OSC inhibitors may be found in WO1996/011021A1, "Substituted heterobicyclic alkyl amines and their use as squalene oxide cyclase inhibitors" and EP1346994A1, "cholesterol biosynthesis inhibitors containing as the active ingredient tricyclic spiro compounds." Those compounds may be tested as disclosed herein for anticancer activity.

Inhibition of OSC as a Strategy for the Treatment of Cancers

The effect of potent OSC inhibitors, including Ro 48-8071, on the viability of cancer cells was evaluated; these inhibitors were shown to achieve potent similar to the effects of PRIMA-1 on breast cancer cells. The sulforhodamine B ('SRB') assay was employed to evaluate viability in the presence and absence of PRIMA-1 and Ro 48-8071 on BT-474 and T47-D breast cancer cells. The sulforhodamine B (SRB) assay was employed to evaluate the effect of OSC inhibitor Ro 48-8071 on viability of breast cancer and normal mammary gland cells with slight modification of the original procedure established at NCI. Accordingly, the cells were seeded in 96-well plates in 100 μl culture medium and incubated overnight at 37° C. with 5% $CO_2$. The culture medium was removed after 24 h, and the attached cells were washed with DMEM/F12 medium and treated by PRIMA-1 or Ro 48-8071 at various concentrations for 24 hrs. The surviving or adherent cells were fixed in situ by withdrawing the growth medium and adding 100 μl of PBS and 100 μl of 50% cold trichloroacetic acid and then incubating at 4° C. for 1 h. The surviving cells were washed with ice-water, dried at room temperature (RT), and then stained with 50 μl 4% SRB for 8 min at RT. Unbound dye was removed by washing 5 times with cold 1% acetic acid, and the plates were dried at RT. Bound stain was solubilized with 150 μl 10 mM Tris buffer, and absorbance of samples were measured at 520 nm with a SpecTRA MAX 190 microplate reader (Sunnyvale, Calif.). In these experiments on BT-474, T47-D, and AG11132A cell lines, six wells were used for each concentration, and each experiment was performed at least twice.

Figure 2A:
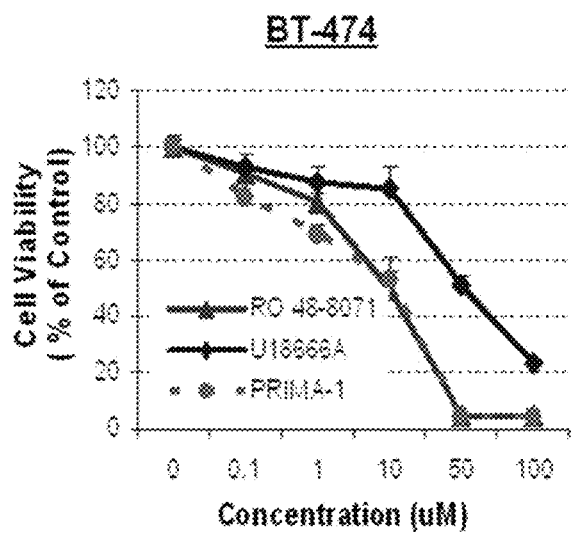
FIG. 2 shows the effect of PRIMA-1, Ro 48-8071, and U18666A on breast cancer cell viability. BT-474 ($1.0 \times 10^4$/well, see FIG. 2A, upper) or T47-D ($0.6 > 10^4$/well, see FIG. 2B, lower) cells were seeded into a 96-well plate overnight, and cells were washed and treated with the indicated concentration of Ro 48-8071 or PRIMA-1 for 24 hours. Cell growth and viability were determined by the SRB assay described in Methods. The OSC-inhibitors Ro 48-8071, PRIMA-1, and U18666A significantly inhibit the viability of BT-474 and T-47-D cells in a dose-dependent manner.
Figure 2B:
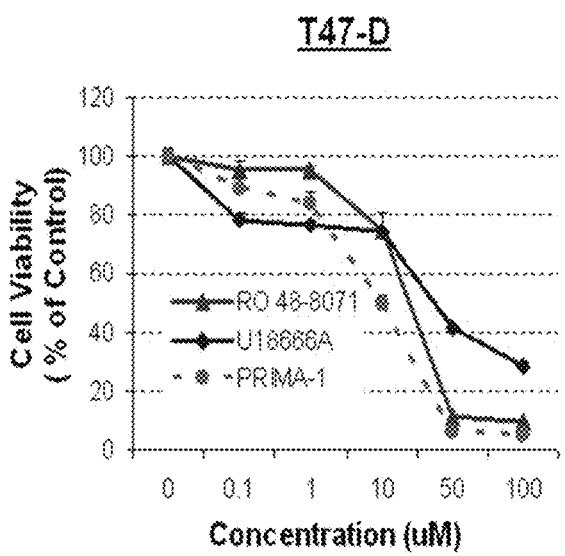
Figure 3:
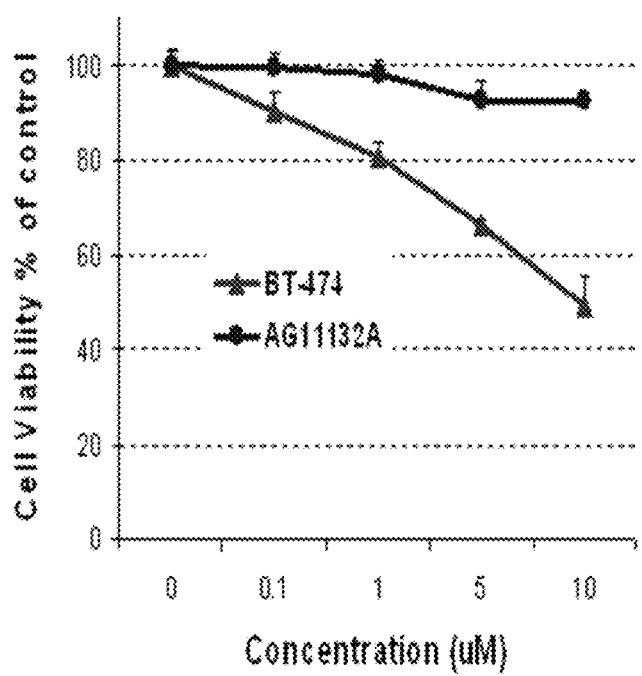
FIG. 3 shows the effect of Ro 48-8071 on breast cancer and normal mammary cell viability. BT-474 ($1.0 \times 10^4$/well) and AG11132A cells ($0.7 \times 10^4$/well) were seeded into a 96-well plate overnight, and cells were washed and treated with the indicated concentration of Ro 48-8071 for 24 hours. There is significantly less inhibition of normal mammary AG11132A cell viability.

FIG. 2 compares the viability of tumor cells (BT-474 in FIG. 2A, and T47-D in FIG. 2B) in the presence of increasing concentrations of PRIMA-1, Ro 48-8071, and U18666A. The SRB assay revealed that the potent inhibitors of OSC, Ro 48-8071 and U18666A, dramatically suppresses the cell growth of both tumor cell lines and exhibits a dose-response relationship similar to that of PRIMA-1. The effective in vitro dosage of Ro 48-8071 is between 0.1 μM and 25 μM for BT-474 cells and T47-D cells with 24 hours of treatment.

The effects of Ro 48-8071 were also compared on the viability of BT-474 tumor cell line and the normal mammary cell line AG11131A. FIG. 4 shows the selective loss of viability of the breast tumor cells compared to normal mammary cells in the presence of Ro 48-8071.

The effect of OSC inhibition was evaluated in additional cancer cell lines as well. Cancer cell lines may be purchased from ATCC (Manassas, Va.). The SRB assay has been employed for determination of the inhibitory effects of RO 48-8071 on growth of different cancer cells. Cells were seeded into 96-well plates and incubated overnight at 37° C. with 5% $CO_2$. The culture medium was removed after 24 hours, and cells were washed with DMEM/F12 medium and then treated with various concentrations of RO 48-8071 in 5% FBS culture medium for 24 and 48 hours. Surviving or adherent cells were fixed in situ by withdrawing the growth medium, adding 100 μl PBS and 100 μl 50% trichloroacetic acid and then incubating at 4° C. for one hour. Cells were washed with ice-cold water, dried at room temperature (RT), and then stained with 50 μl 4% SRB for eight minutes at RT. Unbound dye was removed by washing with cold 1% acetic acid for five times, and plates were dried at RT. Bound stain was solubilized with 150 μl 10 mM Tris buffer and absorbance of samples was read at 520 nm with a SpecTRA MAX 190 microplate reader (Molecular Devices, Sunnyvale, Calif.). Six wells were used for each concentration, and each experiment was performed two to three times.

Figure 4A:
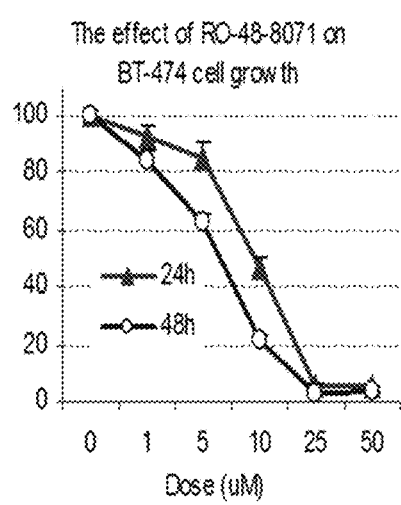
FIG. 4 shows the effects of RO 48-8071 on the viability of breast cancer cell lines BT-474 (see FIG. 4A, upper left), T47-D (see FIG. 4B, upper right), and MCF-7 (see FIG. 4C, bottom), over 24 and 48 hours.

Effect of RO 48-8071 on breast cancer cell line BT-474 viability. Refer to FIG. 4A, which shows the effects of Ro 48-8071 on breast cancer (BT-474) cell growth after 24 and 48 hours treatments. The culture mediums employed 10% FBS DMEM/F12 for culture and 5% FBS DMEM/F12 for treatment.

Figure 4B:
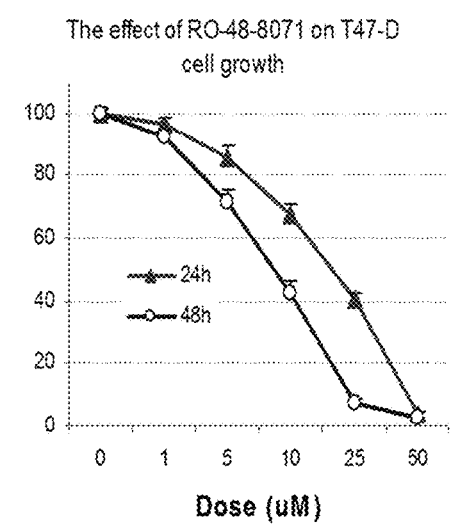

Effect of RO 48-8071 on breast cancer cell line T47-D viability. Refer to FIG. 4B, which shows the effects of Ro 48-8071 on breast cancer (T47-D) cell growth after 24 and 48 hours treatments. The culture mediums employed 10% FBS DMEM/F12 for culture and 5% FBS DMEM/F12 for treatment.

Figure 4C:
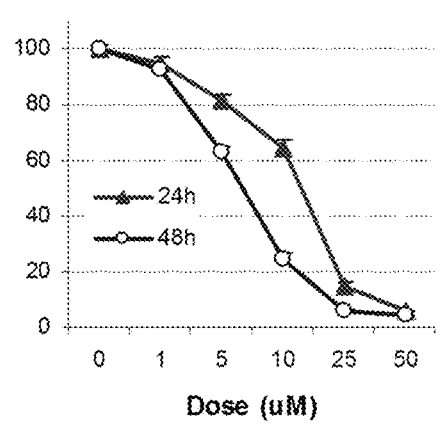

Effect of RO 48-8071 on breast cancer cell line MCF-7 viability. Refer to FIG. 4C, which shows the effects of Ro 48-8071 on breast cancer (MCF-7) cell growth after 24 and 48 hours treatments. The culture mediums employed 10% FBS DMEM/F12 and 10 µg/ml insulin for culture and 5% FBS DMEM/F12 for treatment.

Figure 5A:
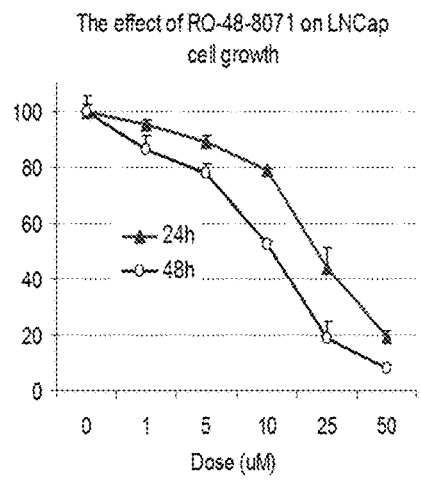
FIG. 5 shows the effects of RO 48-8071 on the viability of prostate cancer cell lines LNCaP (see FIG. 5A, upper left), PC-3 (see FIG. 5B, upper right), and DU145 (see FIG. 5C, bottom) over 24 and 48 hours.

Effect of RO 48-8071 prostate cancer cell line LNCaP viability. Refer to FIG. 5A, which shows the effects of Ro 48-8071 on prostate cancer (LNCaP) cell growth after 24 and 48 hours treatments. The culture mediums employed 20% FBS RPMI-1640 for culture and 10% FBS RPMI-1640 for treatment.

Figure 5B:
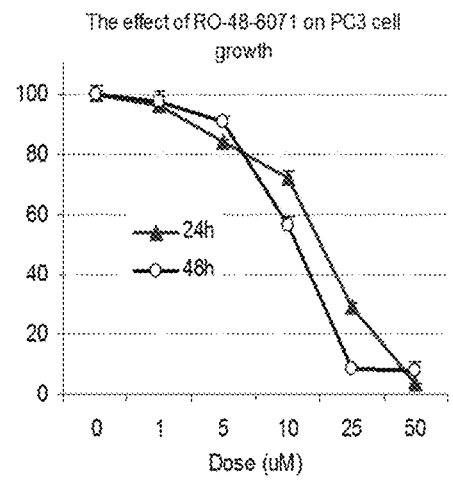

Effect of RO 48-8071 on prostate cancer cell line PC-3 viability. Refer to FIG. 5B, which shows the effects of Ro 48-8071 on prostate cancer (PC-3) cell growth after 24 and 48 hours treatments. The culture mediums employed 10% FBS RPMI-1640 for culture and 5% FBS RPMI-1640 for treatment.

Figure 5C:
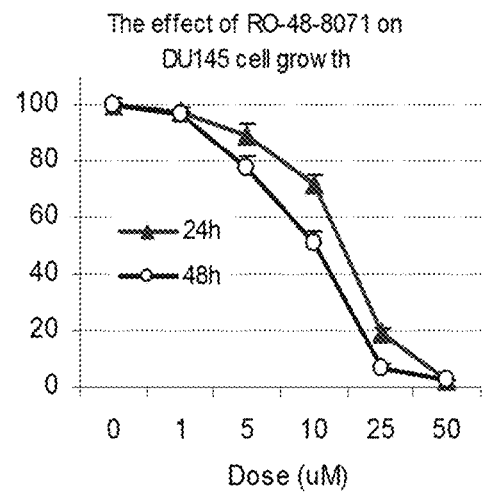

Effect of RO 48-8071 on prostate cancer cell line DU145 viability. Refer to FIG. 5C, which shows the effects of Ro 48-8071 on prostate cancer (DU145) cell growth after 24 and 48 hours treatments. The culture mediums employed 10% FBS EMEM for culture and 5% FBS EMEM for treatment.

Figure 6A:
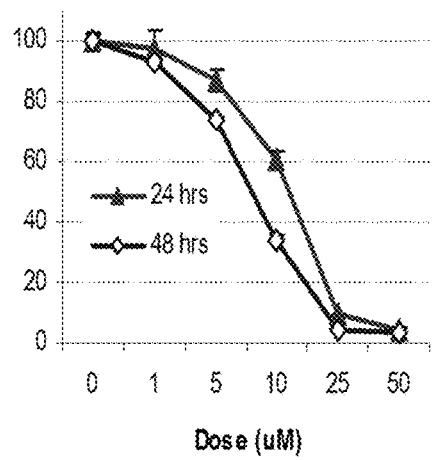
FIG. 6 shows the effects of RO 48-8071 on the viability of colon cancer cell lines DLD-1 (see FIG. 6A, upper left) and LoVo (see FIG. 6B, upper right), and ovarian cancer cell lines OVCAR-3 (see FIG. 6C, lower left) and SK-OV-3 (see FIG. 6D, lower left) over 24 and 48 hours.

Effect of RO 48-8071 on colon cancer cell line DLD-1 viability. Refer to FIG. 6A, which shows the effects of Ro 48-8071 on colon cancer (DLD-1) cell growth after 24 and 48 hours treatments. The culture mediums employed 10% FBS RPMI-1640 for culture and 5% FBS RPMI-1640 for treatment.

Figure 6B:
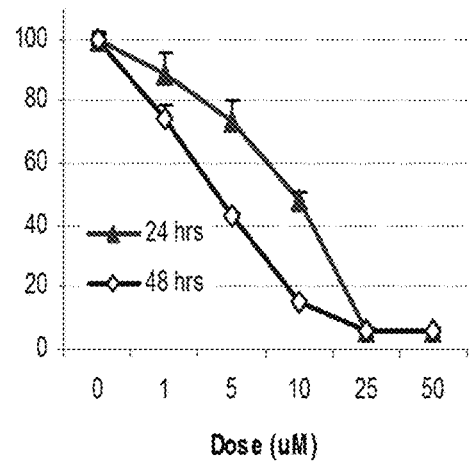

Effect of RO 48-8071 on colon cancer cell LoVo viability. Refer to FIG. 6B, which shows the effects of Ro 48-8071 on breast cancer (LoVo) cell growth after 24 and 48 hours treatments. The culture mediums employed 10% FBS F-12K for culture and 5% FBS F-12K for treatment.

Figure 6C:
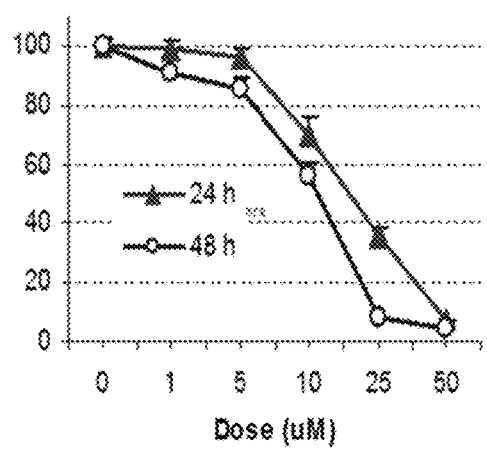

Effect of RO 48-8071 on ovarian cancer cell line OVCAR-3 viability. Refer to FIG. 6C, which shows the effects of Ro 48-8071 on ovarian cancer (OVCAR-3) cell growth after 24 and 48 hours treatments. The culture mediums employed 20% FBS RPMI-1640 for culture and 10% FBS RPMI-1640 for treatment.

Figure 6D:
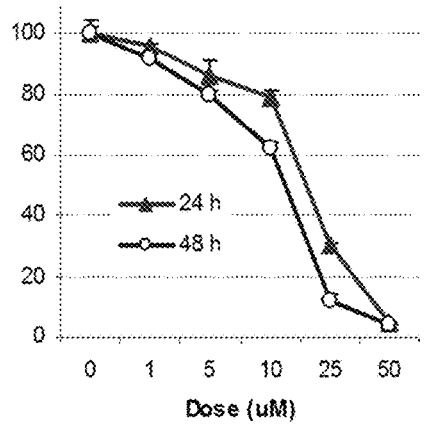

Effect of RO 48-8071 on ovarian cancer cell line SK-OV-3 viability. Refer to FIG. 6D, which shows the effects of Ro 48-8071 on ovarian cancer (SK-OV-3) cell growth after 24 and 48 hours treatments. The culture mediums employed 10% FBS McCoy's 5a for culture and 5% FBS McCoy's 5a for treatment.

Figure 7A:
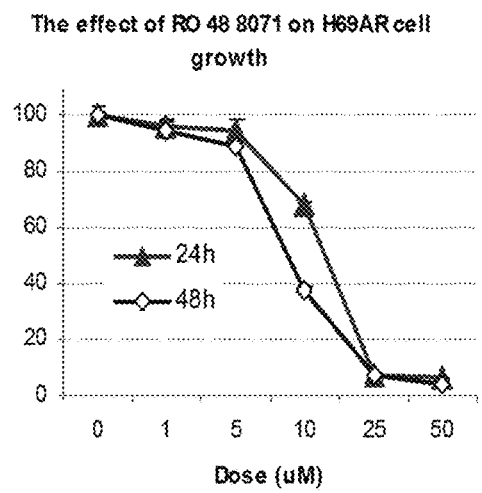
FIG. 7 shows the effects of RO 48-8071 on the viability of lung cancer cell line H69AR (see FIG. 7A, upper left), NCI-H23 (see FIG. 7B, upper right), and A549 (see FIG. 7C, bottom) over 24 and 48 hours.

Effect of RO 48-8071 on lung cancer cell line H69AR viability. Refer to FIG. 7A, which shows the effects of Ro 48-8071 on breast cancer (H69AR) cell growth after 24 and 48 hours treatments. The culture mediums employed 20% FBS RPMI-1640 for culture and 10% FBS RPMI-1640 for treatment.

Figure 7B:
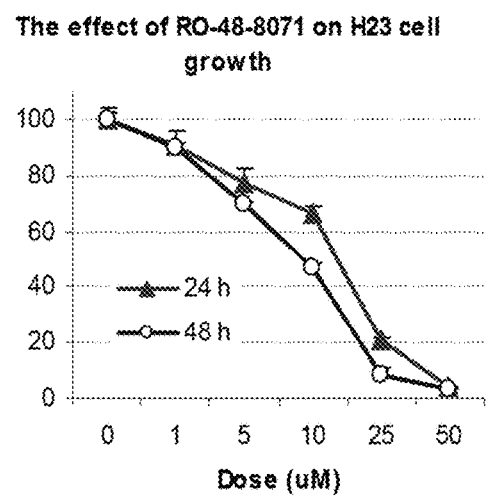

Effect of RO 48-8071 on lung cancer cell line H23 viability. Refer to FIG. 7B, which shows the effects of Ro 48-8071 on lung cancer (NCI-H23) cell growth after 24 and 48 hours treatments. The culture mediums employed 10% FBS RPMI-1640 for culture and 5% FBS RPMI-1640 for treatment.

Figure 7C:
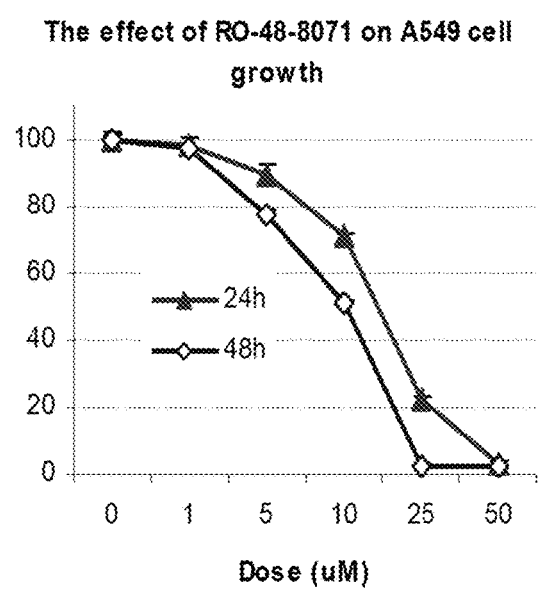

Effect of RO 48-8071 on lung cancer cell line A549 viability. Refer to FIG. 7C, which shows the effects of Ro 48-8071 on lung cancer (A549) cell growth after 24 and 48 hours treatments. The culture mediums employed 10% FBS F-12K for culture and 5% FBS F-12K for treatment.

Effect of RO 48-8071 on pancreatic cancer cell line Capan-1 viability. Refer to FIG. 8A, which shows the effects of Ro 48-8071 on pancreatic cancer (Capan-1) cell growth after 24 and 48 hours treatments. The culture mediums employed 20% FBS IMDM for culture and 10% FBS IMDM for treatment.

Effect of RO 48-8071 on pancreatic cancer cell line BxPC-3 viability. Refer to FIG. 8B, which shows the effects of Ro 48-8071 on pancreatic cancer (Bx-PC-3) cell growth after 24 and 48 hours treatments. The culture mediums employed 10% FBS RPMI-1640 for culture and 5% FBS RPMI-1640 for treatment.

Figure 9A:
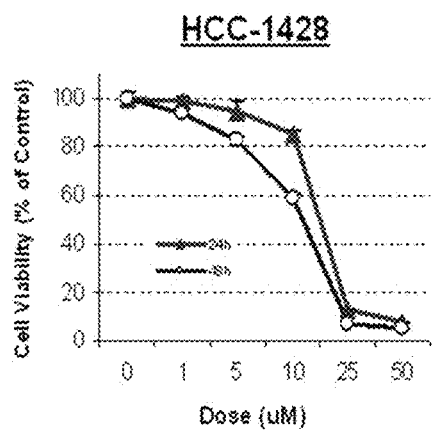
FIG. 9 shows the effects of RO 48-8071 on the viability of estrogen, progesterone, and HER-2/neu receptors positive breast cancer cell lines HCC-1428 (see FIG. 9A, upper left) and ZR-75 (see FIG. 9B, upper right), and Estrogen, progesterone, and HER-2/neu receptors negative breast cancer cell lines MDA-231 (see FIG. 9C, lower left) and BT20 (see FIG. 9D, lower left) over 24 and 48 hours.
Figure 9B:
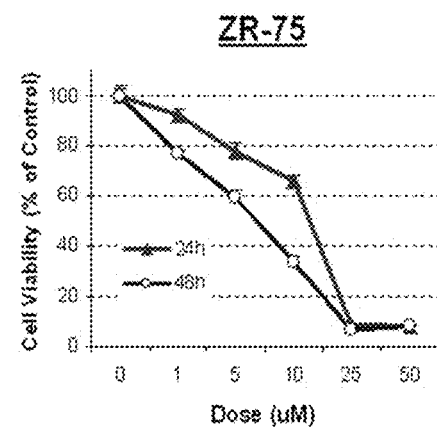

Effect of RO 48-8071 on estrogen, progesterone, and HER-2/neu receptors positive breast cancer cell line HCC-1428 and ZR-75 viability. Refer to FIGS. 9A and 9B, respectively, which show the effects of Ro 48-8071 on pancreas cancer (HCC-1428 and ZR-75) cell growth after 24 and 48 hours treatments. The culture mediums employed 10% FBS RPMI-1640 for culture and 5% FBS RPMI-1640 for treatment.

Figure 9C:
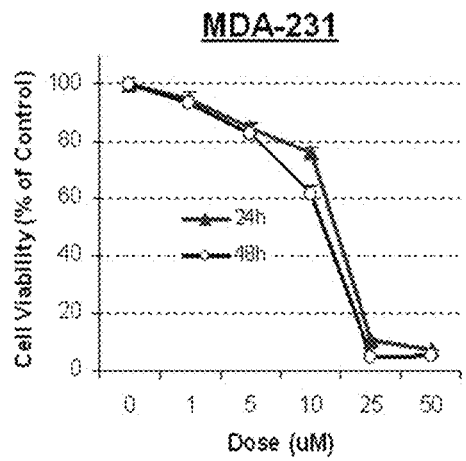
Figure 9D:
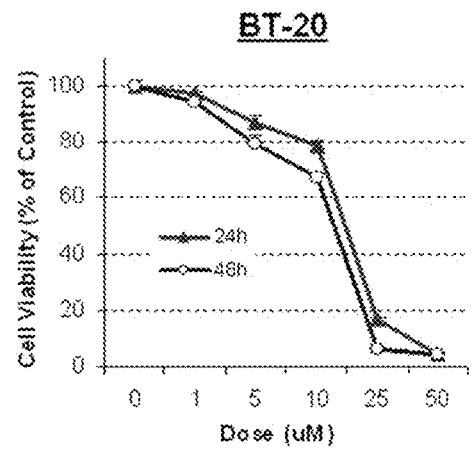
Figure 10A:
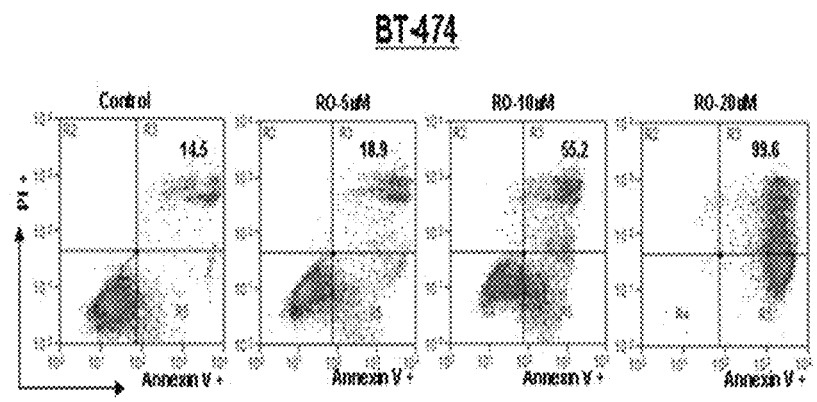
FIG. 10 shows the results of an apoptosis assay in estrogen receptor, progesterone receptor, and HER-2/neu receptor negative (FIGS. 10A and 10B, respectively) and estrogen receptor, progesterone receptor, and HER-2/neu receptor positive cells (10C and 10D, respectively) human breast cancer cells. BT-474 (FIG. 10A), MCF-7 (FIG. 10B), BT-20 (FIG. 10C), and MDA-231 (FIG. 10D) cells were stained for early apoptosis (annexin V) and late apoptosis/cell death (propidium iodide) markers. Quadrant R5 shows annexin V positive cells and quadrant R3 shows annexin V plus propidium iodide positive cells.
Figure 10B:
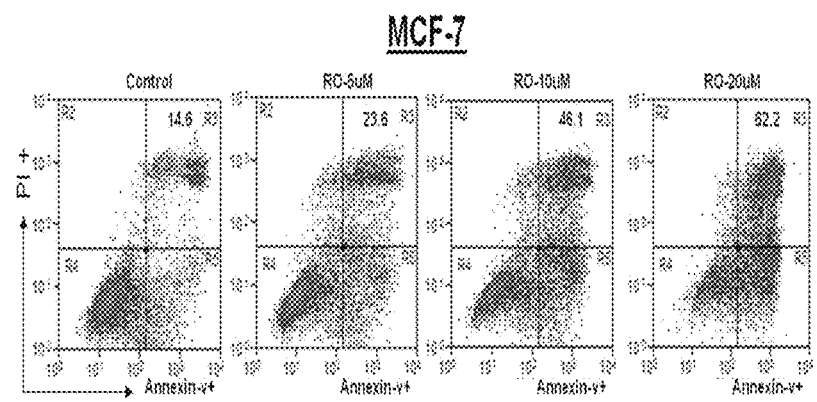
Figure 10C:
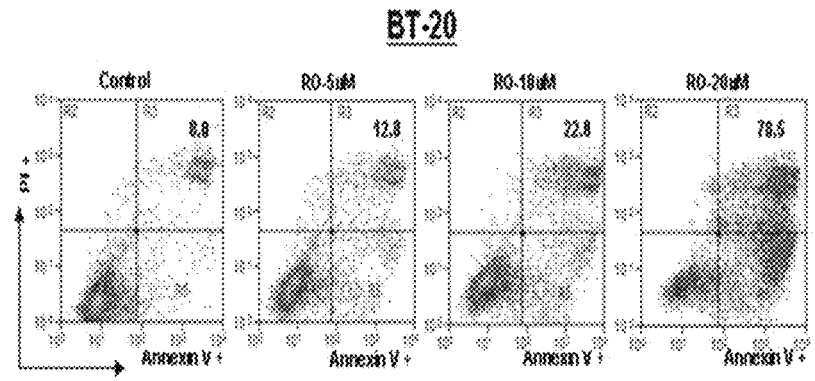
Figure 10D:
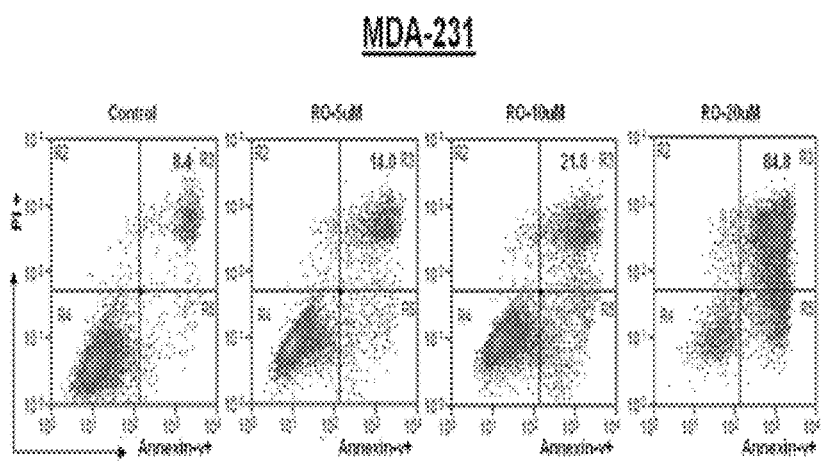

Effect of RO 48-8071 on estrogen, progesterone, and HER-2/neu receptors negative breast cancer cell line MDA-231 and BT-20 viability. Refer to FIGS. 9C and 9D, respectively, which show the effects of Ro 48-8071 on pancreas cancer (MDA-231 and BT-20) cell growth after 24 and 48 hours treatments. The culture mediums employed 10% FBS RPMI-1640 for culture and 5% FBS RPMI-1640 for treatment.

Table 2 summarizes the $IC_{50}$ analyses of RO 48-8071 in different cancer cell lines, among which several cell lines are drug resistant phenotypes.

TABLE 2

IC50s of RO 48-8071 on different types of cancers

| Cancers | Cell lines | $IC_{50}$ (µM) (24 hours) | $IC_{50}$ (µM) (48 hours) |
|---|---|---|---|
| Breast (ER+ PR+) | BT-474 | 9.514 ± 0.05 | 6.060 ± 0.233 |
| | T47-D | 11.532 ± 0.358 | 7.760 ± 0.293 |
| | MCF-7 | 12.320 ± 0.585 | 6.335 ± 0.344 |
| | HCC-1428 | 14.644 ± 0.417 | 11.578 ± 0.336 |
| | ZR-75 | 11.038 ± 0.289 | 7.632 ± 0.304 |
| Breast (triple negative) | MDA-231 | 14.975 ± 0.482 | 10.734 ± 0.276 |
| | BT-20 | 15.801 ± 0.335 | 12.674 ± 0.180 |
| Prostate | LNCaP | 18.100 ± 3.22 | 11.754 ± 0.431 |
| | PC-3 | 17.750 ± 1.29 | 11.051 ± 0.350 |
| | DU145 | 13.452 ± 0.895 | 8.614 ± 0.455 |
| Colon | DLD-1 | 11.490 ± 0.243 | 6.925 ± 0.410 |
| | LoVo | 9.461 ± 0.07 | 3.269 ± 0.541 |
| Lung | H69AR | 10.839 ± 0.609 | 8.109 ± 0.355 |
| | NCI-H23 | 14.189 ± 1.277 | 10.280 ± 0.303 |
| | A549 | 13.508 ± 0.928 | 9.255 ± 0.454 |
| Ovary | OV-CAR-3 | 20.511 ± 0.325 | 11.289 ± 0.330 |
| | SK-OV-3 | 18.276 ± 0.639 | 12.717 ± 0.521 |
| Pancreas | Capan-1 | 18.553 ± 1.621 | 13.681 ± 0.168 |
| | BxPC-3 | 11.377 ± 0.621 | 7.108 ± 0.102 |

RO 48-8071 Induces Apoptosis and Cell Death in Human Breast and Prostate Cancer Cells Apoptosis is a normal physiologic process which occurs during embryonic development as well as in maintenance of tissue homeostasis. The apoptotic program is characterized by certain morphologic features, including loss of plasma membrane asymmetry and attachment, condensation of the cytoplasm and nucleus, and internucleosomal cleavage of DNA. Loss of plasma membrane is one of the earliest features. In apoptotic cells, the membrane phospholipid phosphatidylserine (PS) is translocated from the inner to the outer leaflet of the plasma membrane, thereby exposing PS to the external cellular environment. Annexin V is a 35-36 kDa $Ca^{2+}$ dependent phospholipid-binding protein that has a high affinity for PS, and binds to cells with exposed PS. Annexin V may be conjugated to fluorochromes including FITC. This format retains its high affinity for PS and thus serves as a sensitive probe for flow cytometric analysis of cells that are undergoing apoptosis. Since externalization of PS occurs in the earlier stages of apoptosis, FITC Annexin V staining can identify apoptosis at an earlier stage than assays based on nuclear changes such as DNA fragmentation.

FITC Annexin V staining precedes the loss of membrane integrity which accompanies the latest stages of cell death resulting from either apoptotic or necrotic processes. Therefore, staining with FITC Annexin V is typically used in conjunction with a vital dye such as propidium iodide (PI) or 7-Amino-Actinomycin (7-AAD) to allow the investigator to identify early apoptotic cells (PI negative, FITC Annexin V positive). Viable cells with intact membranes exclude PI, wheras the membranes of dead and damaged cells are permeable to PI. For example, cells that are considered viable are FITC Annexin V and PI negative; cells that are in early apoptosis are FITC Annexin V positive and PI negative; and cells that are in late apoptosis or already dead are are both FITC Annexin V and PI positive. This assay does not distinguish between cells that have undergone apoptotic death versus those that have died as a result of a necrotic pathway because in either case, the dead cells will stain with both Annexin-FITC and PI. However, when apoptosis is measured over time, cells can be often tracked from FITC Annexin V and PI negative (viable, or no measurable apoptosis), to FITC Annexin V positive and PI negative (early apoptosis, membrane integrity is present) and finally to FITC Annexin V and PI positive (end stage apoptosis and death). The movement of cells through these three stages suggests apoptosis. In contrast, a single observation indicating that cells are both FITC Annexin V and PI positive, in of itself, reveals less information about the process by which the cells underwent their demise.

BT-474, MCF-7 (estrogen receptor, progesterone receptor, and HER-2/neu receptor positive), BT-20 and MDA-231(estrogen receptor, progesterone receptor, and HER2/neu receptor negative, triple negative) human breast cancer cells, and PC-3 and DU-145 (androgen receptor negative) human prostate cancer cells were used to examine the ability of RO 48-8071 to induce cell death. Cells were seeded in 6 well-plate overnight in DMEM/F12+10% FBS with $1.5\times 10^5$/well for BT-474 and BT-20 cells; in RPMI-1640 medium+10% FBS with $1.2\times 10^5$/well for PC-3 and DU145 cells. Cells were then washed and treated with indicated concentrations (µM) of RO 48-8071 or vehicle alone in growth medium with 5% FBS for 24 hours. Following incubation with the drug, cells were harvested, washed with 2 ml of 10% FBS growth medium and re-suspended in 500 µl binding buffer provided in Annexin V-FITC Apoptosis Detection Kit (BioVision Research Products, Mountain View, Calif.). 5 µl Annexin V and 5 µl propidium iodide (PI) were added to each sample. FACScan flow cytometry (Becton Dickinson, Franklin lakes, N.J.) was used with 10,000 cells per treatment and the percentage Annexin V positive and PI positive cells were quantitated. Quadrant R5 shows Annexin V positive cells and quadrant R3 shows Annexin V plus PI positive cells. Bar graphs from representative experiments show Annexin V positive plus PI positive cells (total dead cells) from tumor cell lines. *Significant differences ($p<0.05$, ANOVA) compared with control group. Experiments were conducted 2-4 times and each treatment was analyzed in triplicate.

In Vivo Studies

Breast Cancer

The exemplary inhibitor, Ro 48-8071, has also been evaluated in vivo and found to inhibit growing of human breast cancer xenografts in nude mice without toxicity. See, e.g., FIGS. 9 and 10.

Female athymic nu/nu nude mice, 5 to 6 weeks-old (18-22 g) were purchased from Harland Sprague-Dawley, Inc. Nude mice were inoculated with 17-β-Estradiol pellets (1.7 mg/pellet, 60 days release) 48 hours before inoculating tumor cells. BT-474 human breast cancer cells, $5\times 10^6$ in 0.15 ml solution mixed with matrigel and DMEM/F12 medium (4/1, v/v) were injected into each flank of mouse subcutaneously and both flanks of each mouse were injected. When tumor volume reached around 100 mm3, animal were randomly assigned to three groups and the treatment started with RO 48-8071 (5 mg/kg/day or 10 mg/kg/day) via tail-vein injection for five days, followed by same treatment every other day for five additional times as shown in the FIG. 13A. Animals in control group received the vehicle alone under identical conditions. Tumor volumes were measured by a digital caliper and calculated using the formula (L×W×H)×0.5236. Significant differences were observed compared with control group ($P<0.05$, using ANOVA).

Figure 13B:
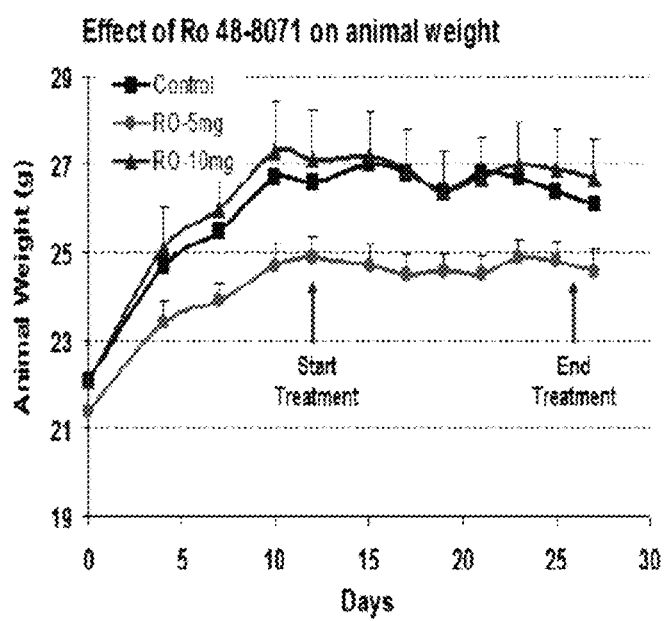
FIG. 13B shows the effects of RO 48-8071 on animal weight of tumor-bearing nude mice.
Figure 14A:
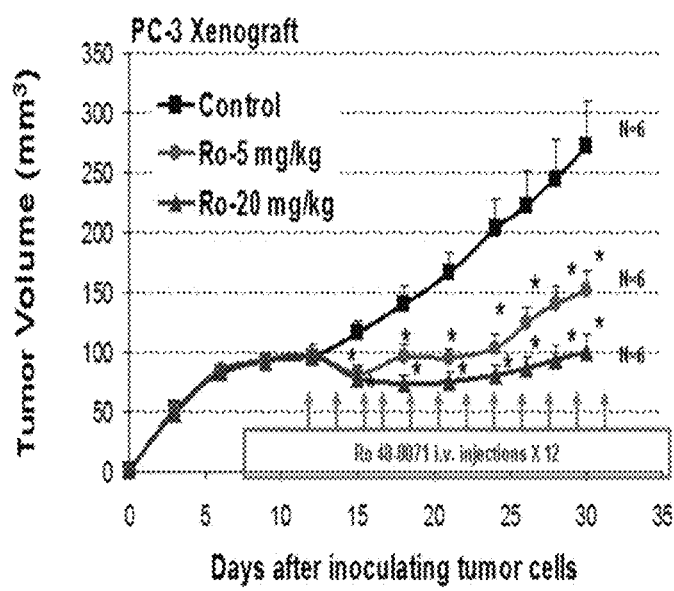
FIG. 14A shows RO 48-8071 suppressing the growth of xenograft prostate tumor (PC-3) in vivo.

Animal weight was monitored throughout the experiment. As shown in FIG. 13B, arrows indicate duration of treatment with RO 48-8071. No significant difference was observed between control and treated groups, which further indicates the OSC inhibitor RO 48-8071 is non-toxic in tumor-bearing nude mice at doses used for inhibiting tumor growth.

Prostate Cancer

Male athymic nu/nu nude mice, 6 weeks-old (21-25 g) were purchased from Harlan Laboratories, Inc. Human prostate cancer PC-3 cells, 5×106 in 0.15 ml solution mixed with matrigel and DMEM/F12 medium (1/1, v/v) were injected into each flank of mouse subcutaneously, and both flanks of each mouse were injected. When tumor volume reached around 100 mm3, animals were randomly assigned to three groups and the treatment started with Ro 48-8071 (5 mg/kg/day or 20 mg/kg/day) via tail-vein injection for five days, followed by same treatment every other day for seven additional times as shown in the FIG. 14A. Animals in control group received the vehicle alone under identical conditions. Tumor volumes were measured every three days by a digital caliper and calculated using the formula (L×W×H)×0.5236. *Significant differences compared with control group ($P<0.05$, using ANOVA).

Figure 14B:
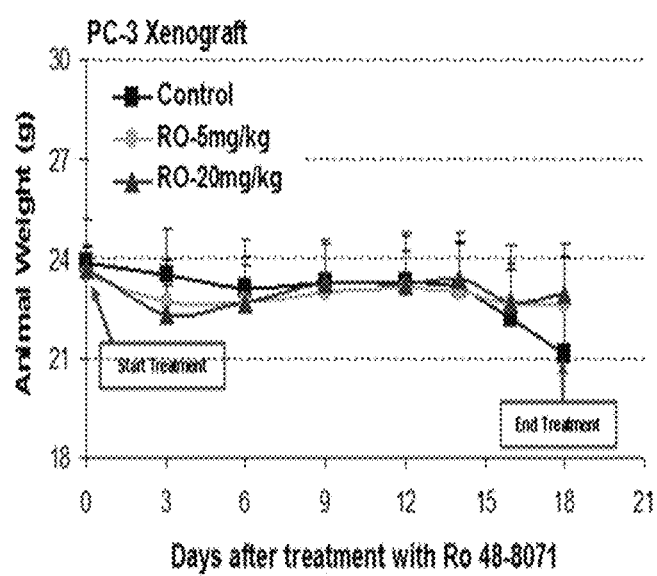
FIG. 14B shows the effects of RO 48-8071 on animal weight of tumor-bearing nude mice.

Animal weight following Ro 48-8071 treatment is shown. As shown in FIG. 14B, arrows indicate duration of treatment with Ro 48-8071. No significant difference was observed between control and treated groups, which further indicates the OSC inhibitor RO 48-8071 is non-toxic in tumor-bearing nude mice at doses used for inhibiting tumor growth.

Additional embodiments are also described in "An inverse docking approach for identifying new potential anti-cancer targets", which is hereby incorporated in its entirety.[18]

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

REFERENCES

[1] Abe I, Rohmer M., Prestwich G D. Enzymatic cyclization of squalene and oxidosqualene to sterols and triterpenes. *Chem. Rev.* 1993, 90:2189-2206.
[2] Wendt K U, Schulz G E, Corey E J, Liu D R. Enzyme mechanisms for polycyclic triterpene formation. *Angew. Chem., Int. Ed.* 2000, 39:2812-2833.
[3] Morand O H, Aebi J, Guerry P, Hartman P G, Hennes U, Himber J, Ji Y H, Jolidon S, Lengsfeld H. Potent inhibitors of mammalian 2,3-oxidosqualene: lanosterol cyclase are orally active cholesterol lowering agents. *Atherosclerosis* 1994, 109 (suppl):321.
[4] Lenhart A, Reinert D J, Aebi J D, Dehmlow H, Morand O H, Schulz G E. Binding Structures and Potencies of oxidosqualene cyclase inhibitors with the homologous squalene-hopene cyclase. *J. Med. Chem.* 2003, 46:2083-2092.
[5] Morand O H, Aebi J D, H D, Ji Y H, N G, Lengsfeld H, Himber J: Ro 48-8071, a new 2,3-oxidosqualene:lanosterol cyclase inhibitor lowering plasma cholesterol in hamsters, squirrel monkeys, and minipigs: comparison to simvastatin. *J. Lipid. Res.* 1997, 38:373-390.
[6] Levine A J, p53, the cellular gatekeeper for growth and division. Cell 1997, 88: 323-331,
[7] Barnes D M, Camplejohn R S. p53, apoptosis, and breast cancer. J. Mammary Gland Biol. Neoplasia 1996, 1:163-175.
[8] Nigro J M, Baker S J. Preisinger A C, et al. Mutations in the p53 gene occur in diverse human tumor types. Nature 1989, 342:705-708.
[9] Bykov V J, Issaeva N, Shilov A, Hultcrantz M, Pugacheva E, Chumakov P, Bergman J, Wiman K G, Selivanova G. Restoration of the tumor suppressor function to mutant p53 by a low molecular-weight compound. *Nat Med* 2002, 8:282-288.
[10] Liang Y, Wu J, Stancel G M, Hyder S M. p53-dependent inhibition of progestin-induced VEGF expression in human breast cancer cells. *J. Steroid Biochem. Mol. Bio.* 2005, 93:173-182.
[11] Liang Y, Besch-Williford C, Hyder S M. PRIMA-1 inhibits growth of breast cancer cells by re-activating mutant p53 protein. *Intl J. Oncol.* 2009, 35:1015-1023.
[12] Huang S-Y, Zou X. An iterative knowledge-based scoring function to predict protein-ligand interactions: I. derivation of interaction potentials. *J. Comput. Chem.* 2006, 27:1865-1875.
[13] Huang S-Y, Zou X. An iterative knowledge-based scoring function to predict protein-ligand interactions: II. validation of the scoring function. *J. Comput. Chem.* 2006, 27:1876-1882.
[14] Huang S-Y, Zou X. Ensemble docking of multiple protein structures: considering protein structural variations in molecular docking. *Proteins* 2007, 66:399-421.
[15] Huang S-Y, Zou X. Efficient molecular docking of NMR structures: application to HIV-1 protease. *Protein Sci.* 2007, 16:43-51.
[16] http://zoulab.dalton.missouri.edu/software.htm
[17] Gao Z, Li H, Zhang H, Liu X, Kang L, Luo X, Zhu W, Chen K, Wang X, Jiang H. PDTD: a Web-Accessible Protein Database for Drug Target Identification. *BMC Bioinform.* 2008, 9:104 (pp 1-7). (http://www.dddc.ac.cn/pdtd).
[18] Grinter S Z, Liang Y, Huang S-Y, Hyder S M, Zou X. An inverse docking approach for identifying new potential anti-cancer targets. J. Mol. Graphics Model. 2011, 29:795-799.
[19] Beltowski, J et al. (2009) Adverse effects of statins-mechanisms and consequences. Curr. Drug Saf. 4:209-228.
[20] Cenedella R J et al., "Direct perturbation of lens membrane structure may contribute to cataracts caused by U18666A, an oxidosqualene cyclaseinhibitor," *J Lipid Res.* July 2004; 45(7):1232-41.

What is claimed is:

1. A method of treating cancer comprising the step of administering to a patient in need thereof a therapeutically effective amount of an inhibitor of a protein target other than HMG-CoA reductase in the cholesterol biosynthetic pathway, wherein the inhibitor is a compound having the formula of Formula I:

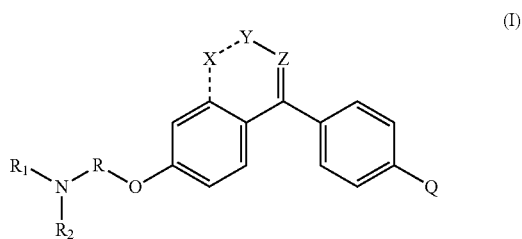

or a salt thereof, wherein:
X is chosen from hydrogen, halogen, O, $NR_3R_4$, S, CH2, and CH;
Y is chosen from null, a bond, O and CH;
Z is chosen from O, N, and CH;
dashed bonds may be present or absent if present, the bond may be single or double as valency allows;
R, $R_1$ and $R_2$ are independently chosen from alkyl, alkene, aryl, alkyne, cycloalkyl, and alkylcycloalkylalkyl, any of which may be optionally substituted;
$R_3$ and $R_4$ are independently chosen from a bond, hydrogen, lower alkyl, lower alkene, lower alkyne, aryl, and cycloalkyl, any of which may be optionally substituted; and
Q is chosen from bromine, chlorine and fluorine; and wherein the compound is not PRIMA-1, wherein said protein target is oxidosqualene cyclase and wherein said cancer has cells selected from the group consisting of:
a) cancer cells that do not have a p53 mutation;
b) breast cancer cells which are HER2/neu positive
c) breast cancer cells which are estrogen receptor and progesterone receptor positive;

d) breast cancer cells which are triple negative for estrogen receptor, progesterone receptor, and HER2/neu; and e) cancer cells that undergo apoptosis.

2. The method as recited in claim 1, wherein the cancer is chosen from cancers of the breast, prostate, lung, colon, ovary, pancreas, liver, thyroid, stomach, uterine, lymphoma, brain, skin, kidney, mouth, throat, tongue, and bladder, as well as leukemia, and the drug resistant phenotypes thereof.

3. The method as recited in claim 1, wherein the cancer cells do not have a p53 mutation.

4. The method as recited in claim 1, wherein the cancer cells are breast cancer cells which are HER2/neu positive.

5. The method as recited in claim 1, wherein the cancer cells are breast cancer cells which are estrogen receptor and progesterone receptor positive.

6. The method as recited in claim 1, wherein the cancer cells are breast cancer cells which are triple negative for estrogen receptor, progesterone receptor, and HER2/neu.

7. The method as recited in claim 1, wherein the cancer cells undergo apoptosis.

8. The method of claim 1, whereas the compound is 4'-[6-(Allylmethylamino)hexyloxy]-4-bromo-2'-fluorobenzophenone fumarate.

9. A method of reducing cancer cell viability comprising the step of inhibiting the activity of a protein target other than HMG-CoA reductase in the cholesterol biosynthetic pathway of a cell, wherein the step of inhibiting is accomplished with a compound that is not PRIMA-1 and that has the formula of Formula I:

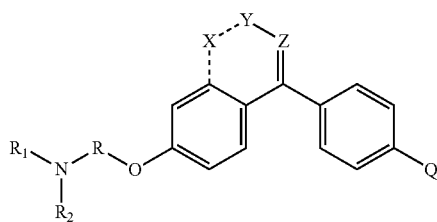

or a salt thereof, wherein:

X is chosen from hydrogen, halogen, O, $NR_3R_4$, S, CH2, and CH;

Y is chosen from null, a bond, O and CH;

Z is chosen from O, N, and CH;

dashed bonds may be present or absent if present, the bond may be single or double as valency allows;

R, $R_1$ and $R_2$ are independently chosen from alkyl, alkene, aryl, alkyne, cycloalkyl, and alkylcycloalkylalkyl, any of which may be optionally substituted;

$R_3$ and $R_4$ are independently chosen from a bond, hydrogen, lower alkyl, lower alkene, lower alkyne, aryl, and cycloalkyl, any of which may be optionally substituted; and Q is chosen from bromine, chlorine and fluorine, wherein said protein target is oxidosqualene cyclase, and wherein said cancer cells are selected from the group consisting of:

a) cancer cells that do not have a p53 mutation;

b) breast cancer cells which are HER2/neu positive c) breast cancer cells which are estrogen receptor and progesterone receptor positive;

d) breast cancer cells which are triple negative for estrogen receptor, progesterone receptor, and HER2/neu; and e) cancer cells that undergo apoptosis.

10. The method as recited in claim 9, wherein the cells are chosen from breast, prostate, lung, colon, ovary, pancreas, liver, thyroid, stomach, uterine, lymphoma, brain, skin, kidney, mouth, throat, tongue, and bladder cancer cells, as well as leukemia cells, and the drug resistant phenotypes thereof.

11. The method as recited in claim 9, wherein the cells do not have a p53 mutation.

12. The method as recited in claim 9, wherein the cancer cells undergo apoptosis.

13. The method as recited in claim 9, wherein the cancer cells are breast cancer cells which are HER2/neu positive.

14. The method as recited in claim 9, wherein the cancer cells are breast cancer cells which are estrogen receptor and progesterone receptor positive.

15. The method as recited in claim 9, wherein the cancer cells are breast cancer cells which are triple negative for estrogen receptor, progesterone receptor, and HER2/neu.

16. The method of claim 9, whereas the compound is 4'-[6-(Allylmethylamino)hexyloxy]-4-bromo-2'-fluorobenzophenone fumarate (Ro 48-8071).

17. A method of treating a drug-resistant cancer comprising the step of administering a compound which inhibits the activity of oxidosqualene cyclase in the cholesterol biosynthetic pathway to a patient having drug-resistant cancer wherein said cancer has cells selected from the group consisting of:

a) cancer cells that do not have a p53 mutation;

b) breast cancer cells which are HER2/neu positive c) breast cancer cells which are estrogen receptor and progesterone receptor positive;

d) breast cancer cells which are triple negative for estrogen receptor, progesterone receptor, and HER2/neu; and e) cancer cells that undergo apoptosis wherein the step of inhibiting is accomplished with a compound that is not PRIMA-1, and wherein the compound has Formula I:

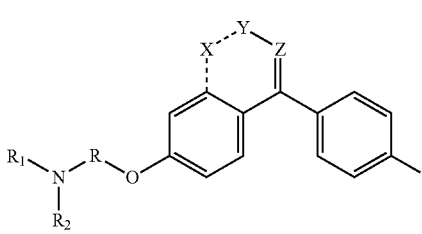

or a salt thereof, wherein:

X is chosen from hydrogen, halogen, O, $NR_3R_4$, S, CH2, and CH;

Y is chosen from null, a bond, O and CH;

Z is chosen from O, N, and CH;

dashed bonds may be present or absent if present, the bond may be single or double as valency allows;

R, $R_1$ and $R_2$ are independently chosen from alkyl, alkene, aryl, alkyne, cycloalkyl, and alkylcycloalkylalkyl, any of which may be optionally substituted;

$R_3$ and $R_4$ are independently chosen from a bond, hydrogen, lower alkyl, lower alkene, lower alkyne, aryl, and cycloalkyl, any of which may be optionally substituted; and Q is chosen from bromine, chlorine and fluorine.

18. The method as recited in claim 17, wherein the drug-resistant cancer is chosen from breast, prostate, lung, colon, ovary, pancreas, liver, thyroid, stomach, uterine, lymphoma, brain, skin, kidney, mouth, throat, tongue, and bladder cancer, as well as leukemia, and a drug resistant phenotype thereof.

19. The method as recited in claim 17, wherein the cells do not have a p53 mutation.

20. The method as recited in claim 17, wherein the cancer cells undergo apoptosis.

21. The method as recited in claim 17, wherein the drug-resistant cancer is breast cancer, the cells of which are HER2/neu positive.

22. The method as recited in claim 17, wherein the drug-resistant cancer is breast cancer, the cells of which are estrogen receptor and progesterone receptor positive.

23. The method as recited in claim 17, wherein the drug-resistant cancer is breast cancer, the cells of which are triple negative for estrogen receptor, progesterone receptor, and HER2/neu.

24. The method of claim 17, whereas the compound is 4'-[6-(Allylmethylamino)hexyloxy]-4-bromo-2'-fluorobenzophenone fumarate (Ro 48-8071).

* * * * *